US010450610B2

(12) United States Patent
Postlethwaite et al.

(10) Patent No.: US 10,450,610 B2
(45) Date of Patent: Oct. 22, 2019

(54) SINGLE NUCLEOTIDE POLYMORPHISMS (SNP) AND ASSOCIATION WITH RESISTANCE TO IMMUNE TOLERANCE INDUCTION

(71) Applicant: University of Tennessee Research Foundation, Knoxville, TN (US)

(72) Inventors: Arnold E. Postlethwaite, Eads, TN (US); Weikuan Gu, Cordova, TN (US)

(73) Assignee: UNIVERSITY OF TENNESSEE RESEARCH FOUNDATION, Konxville, TN (US)

( * ) Notice: Subject to any disclaimer, the term of this patent is extended or adjusted under 35 U.S.C. 154(b) by 25 days.

(21) Appl. No.: 15/183,764

(22) Filed: Jun. 15, 2016

(65) Prior Publication Data

US 2017/0016068 A1    Jan. 19, 2017

Related U.S. Application Data

(63) Continuation of application No. 14/243,998, filed on Apr. 3, 2014, now abandoned, which is a continuation of application No. 13/972,362, filed on Aug. 21, 2013, now abandoned, which is a continuation of application No. 12/988,395, filed as application No. PCT/US2009/041134 on Apr. 20, 2009, now abandoned.

(60) Provisional application No. 61/104,504, filed on Oct. 10, 2008, provisional application No. 61/080,012, filed on Jul. 11, 2008, provisional application No. 61/071,264, filed on Apr. 18, 2008.

(51) Int. Cl.
| | |
|---|---|
| *C12Q 1/6883* | (2018.01) |
| *A61K 39/00* | (2006.01) |
| *A61K 38/39* | (2006.01) |

(52) U.S. Cl.
CPC ............ *C12Q 1/6883* (2013.01); *A61K 38/39* (2013.01); *A61K 39/00* (2013.01); *C12Q 2600/106* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2004/0146870 A1 | 7/2004 | Liao et al. |
| 2005/0227244 A1 | 10/2005 | Matsuzaki et al. |
| 2005/0244421 A1 | 11/2005 | Strittmatter et al. |
| 2006/0178910 A1 | 8/2006 | Eisenberger et al. |
| 2007/0172445 A1 | 7/2007 | Krotzsch Gomez et al. |
| 2008/0064668 A1 | 3/2008 | Uskokovic et al. |
| 2008/0070253 A1 | 3/2008 | Simon Buéla et al. |
| 2008/0070792 A1 | 3/2008 | Stoughton et al. |

OTHER PUBLICATIONS

Kwok, P. (2001) Methods for Genotyping Single Nucleotide Polymorphisms. Annual Review of Genomics and Human Genetics, 2: 235-258.*
Alberts, et al. "Molecular Biology of the Cell, Fifth Edition". New York:Garland Science, 2008. p. 259.*
Hegele, R. (2002) SNP Judgments and Freedom of Association. Arteriosclerosis, Thrombosis, and Vascular Biology, 22:1058-1061.*
Evans et al. (1999) Translating Functional Genomics into Rational Therapeutics. Science, 286:487-491.*
Farh et al. (2015) Genetic and epigenetic fine mapping of causal autoimmune disease variants. Nature, 518:337-343.*
Freeman et al. (1997) DNA by Mail: An Inexpensive and Noninvasive Method for Collecting DNA Samples from Widely Dispersed Populations. Behavior Genetics, 27(3):251-257.*
DbSNP assay ID ss66773469 (accessed from NCBI's dbSNP on Feb. 11, 2013 at http://www.ncbi.nlm.nih.gov/SNP/snp_ss.cgi?subsnp_id=66773469, submitted Nov. 9, 2006).*
Infinium II method description (accessed from NCBI's dbSNP on Feb. 11, 2013 at http://www.ncbi.nlm.nih.gov/SNP/snp_viewTable.cgi?mid=4812, 2 pages).*
Alberts, Bruce et al. "Molecular Biology of the Cell, Fifth Edition," New York: Garland Science, 2008, p. 259.
DbSNP assay ID ss66773469 (accessed from NCBI's dbSNP on Feb. 11, 2013 at <http://www.ncbi.nlm.nih.gov/SNP/snp_ss.cgi?subsnp id=66773469>, submitted Nov. 9, 2006), 1 page.
Freeman, Bernard et al. "DNA by Mail: An Inexpensive and Noninvasive Method for Collecting DNA Samples from Widely Dispersed Populations," Behavior Genetics, 1997, vol. 27, No. 3, pp. 251-257.
International Search Report for PCT/US2009/041134, filed Apr. 20, 2009, dated Dec. 9, 2009, 3 pgs.
Kwok, Pui-Yan "Methods for Genotyping Single Nucleotide Polymorphisms," Annu. Rev. Genomics Hum. Genet., 2001, 2, pp. 235-258.
Infinium II method description (accessed from NCBI's dbSNP on Feb. 11, 2013 at <http://www.ncbi.nlm.nig.gov/SNP/snp_viewTable.cgi?mid=4812> ), 2 pages.
Wood, Kathyrn J. et al. "Alloantigen-induced specific immunological unresponsiveness," Phil. Trans. R. Soc. Lond., B 2001, 356, pp. 665-680.

* cited by examiner

*Primary Examiner* — Neil P Hammell
(74) *Attorney, Agent, or Firm* — Squire Patton Boggs (US) LLP

(57) ABSTRACT

This application discloses methods, systems and kits for correlating the presence or absence of certain nucleic acid sequences within a population with the ability to create immune tolerance in that same population. Tolerance can be induced by solo or repeated administration of antigen, including soluble antigens administered either intravenously or sublingually. This application also discloses methods for detecting variants. In addition the application addresses the use or avoidance of non steroidal anti inflammatory drugs in therapy.

8 Claims, 16 Drawing Sheets

Specification includes a Sequence Listing.

IFN-γ PRODUCTION BY α1(II) STIMULATED SPLEEN CELLS

ORAL CII TREATMENT OF RA PATIENTS MODULATES PBMC IFNg PRODUCTION BY PBMC cally based diseases, including Inflammatory Bowel Disease (Crohn's Disease and Ulcerative Colitis). Other common forms of tolerance induction contemplated in this invention include internasel and IV tolerance induction.

Today genomics is still not used to refine our medical management, despite the large quantities of research into the genome and SNPs. As such, there are few reliable wide-scale assays, kits and methods that examine an individual's genome to find inherited susceptibility, gene expression, and predicted pharmacogenomic response. More specifically, there is no use of genomics in the field of immune tolerance.

The inventors are credited with providing methods, reagents, kits and assays that merge genomics with immune tolerance. As such, the inventors are able to detect nucleic acid sequences, and based on the presence and/or absence of nucleic acid sequences; tailor a method of care for the patient who desires induction of immune tolerance. In one specific embodiment, the nucleic acid sequences of interest are SNPs.

SUMMARY OF THE INVENTION

The present invention relates to correlating the presence or absence of certain nucleic acid sequences within a population with the ability to create immune tolerance in that same population. This correlation may be used to assist with induction of immune tolerance. In some embodiments, the invention concerns tolerance induced by repeated administration of very large doses of antigen, or of small doses that are below the threshold required for stimulation of an immune response. In some embodiments, tolerance is most readily induced by soluble antigens administered either intravenously or sublingually. Furthermore, it's contemplated that immunosuppression also facilitates the induction of tolerance. Based on the correlation of the presence or absence of certain nucleic acid sequences associated with specific diseases or disorders, the present invention also provides for methods of detecting variants. In one specific embodiment, the nucleic acid sequences of interest are SNPs. In addition embodiments of the invention address the use or avoidance of non steroidal anti inflammatory drugs in therapy.

The invention includes a method for screening for susceptibility to immune tolerance development, comprising screening for at least one SNP. The method of screening may include FISH, use of a DNA array, and/or hybridizing a polynucleotide probe.

The invention includes a method for screening for susceptibility to immune tolerance development, including use of allele-specific probe hybridization, allele-specific primer extension, allele-specific amplification, sequencing, 5' nuclease digestion, molecular beacon assay, oligonucleotide ligation assay, size analysis, and/or single-stranded conformation polymorphism.

The invention includes a method for screening for susceptibility to immune tolerance development, including correlating the presence or absence of the at least one SNP with ability of a host to develop immune tolerance as a result of administration of one or more antigens or therapeutic agents to the host. The antigen may be collagen, including collagen selected from the group types consisting of I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII and XXVIII.

The invention includes a method for screening for susceptibility to immune tolerance development, including obtaining a sample from said host comprising nucleic acid; isolating nucleic acid from said sample; assaying said sample for the presence or absence of at least one SNP, wherein the presence or absence of the at least one SNP is indicative of an increased susceptibility to develop immune tolerance. The sample may be whole blood, blood plasma, urine, tears, semen, saliva, buccal mucosa, interstitial fluid, lymph fluid, meningeal fluid, amniotic fluid, glandular fluid, sputum, feces, perspiration, mucous, vaginal secretion, cerebrospinal fluid, hair, skin, fecal material, wound exudate, wound homogenate, and wound fluid. Further, the method may include induction of immune tolerance by administration of at least one antigen to the host, where the antigen can be a type of collagen.

The immune tolerance may be to any autoimmune disease such as sclerotic disease like systemic sclerosis.

The invention includes a method for screening for susceptibility to immune tolerance development, including use of one or more computer programs for use with at least one computer system, where computer program includes a plurality of instructions including at least one instruction for aiding in identification of the presence or absence of said at least one SNP; at least one instruction for associating the presence or absence of said at least one SNP with at least one disease state; and at least one instruction for correlating the presence or absence of said at least one SNP with a score indicating susceptibility of a host to develop immune tolerance. The computer may also generate a report including the results of the plurality of instruction, where the report may be transmitted over a network, on-line portal, by paper or e-mail in a secure or non-secure manner.

The invention includes a method of administering at least one therapeutic agent, the method comprising genotyping one or more SNP(s) in the nucleic acid of a host, correlating the one or more SNP(s) with one or more diseases or disorders, using a mathematical algorithm to determine probability that said host will respond positively or negatively to administration of at least one therapeutic agent, and administrating or not administrating a therapeutic agent to the host based on the results of said mathematical algorithm.

The invention includes a method for conducting a clinical trial in which one or more antigen(s) are evaluated, including genotyping one or more SNP(s) relating to one or more diseases or disorders; analyzing the genotyping results; determining a course of action based on the results of said genotyping, wherein said course of action comprises including individual in the clinical trial based on the results of said genotyping having indicated that said individuals are likely to respond to said one or more antigen(s), and/or excluding individuals from participating in the clinical trial based on the results of said genotyping having indicated that said individuals are not likely to respond to said one or more antigen(s).

The invention includes a method for identifying an individual who has an altered risk for developing an autoimmune disease, comprising detecting a single nucleotide polymorphism (SNP) in SEQ ID NO: 1 in said individual's nucleic acids, wherein the presence of the SNP is correlated with an altered risk for autoimmune disease.

DEFINITIONS

Figure 1:
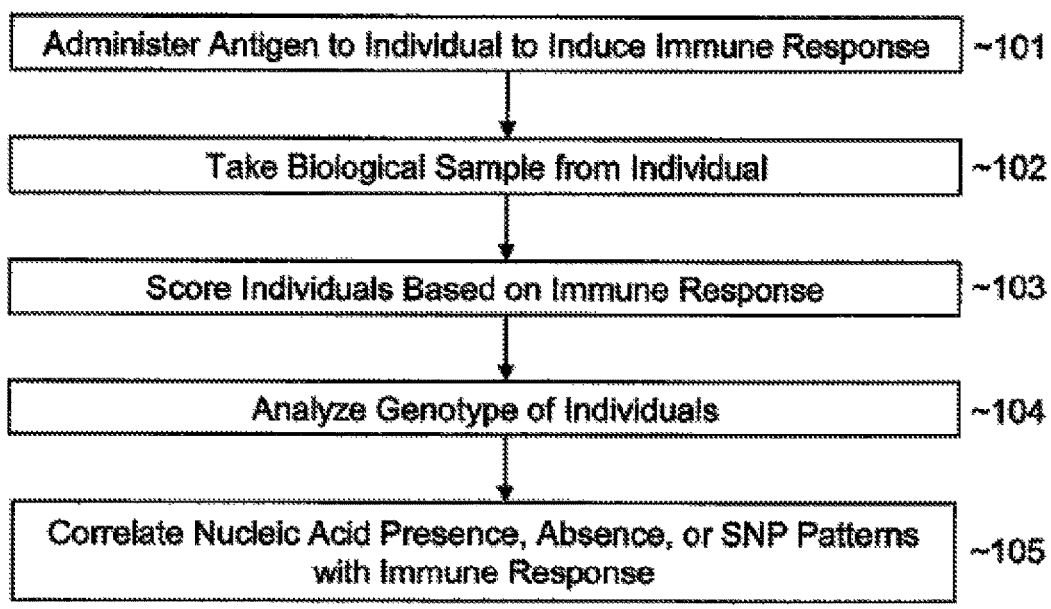
FIG. 1 illustrates a flow chart in accordance with some embodiments of the invention, demonstrating a process of determining if one or more nucleic acids is correlated with induction of immune tolerance.

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions. To assist in describing the invention, the following definitions are provided.

The term "nucleic acid" refers to deoxyribonucleotides or ribonucleotides in either single- or double-stranded form. Those skilled in the art will readily recognize that reference to a particular site on one strand refers, as well, to the corresponding site on a complementary strand. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with "nucleic acid sequence," "gene," "cDNA," and "mRNA" encoded by a gene.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "genotype" as used herein broadly refers to the genetic composition of an organism, including, for example, whether a diploid organism is heterozygous or homozygous for one or more variant alleles of interest.

As used herein, references to "SNPs" and "SNP genotypes" include individual SNPs and/or haplotypes, which are groups of SNPs that are generally inherited together. Haplotypes can have stronger correlations with diseases or other phenotypic effects compared with individual SNPs, and therefore may provide increased diagnostic accuracy in some cases.

The SNPs of the current invention may arise from a substitution of one or more nucleotides for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP may also be a single base insertion or deletion variant.

The SNPs of the current invention may arise from a synonymous codon change, or silent mutation/SNP (terms such as "SNP", "polymorphism", "mutation", "mutant", "variation", and "variant" are used herein interchangeably), is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. SNPs may include all allelics, including bi-, tri-, or tetra-allelics.

In defining a SNP position, SNP allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand to refer to a particular SNP position, SNP allele, or nucleotide sequence. Probes and primers, may be designed to hybridize to either strand and SNP genotyping methods disclosed herein may generally target either strand.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds. References to "polypeptides," "peptides" or "proteins" of the present invention include peptides, polypeptides, proteins, or fragments thereof, that contain at least one amino acid residue that differs from the corresponding amino acid sequence of the art-known peptide/polypeptide/protein (the protein may be interchangeably referred to as the "wild-type", "reference", or "normal" protein). Such variant peptides/polypeptides/proteins can result from a codon change caused by a nonsynonymous nucleotide substitution at a protein-coding position (i.e., a missense mutation) disclosed by the present invention. Variant peptides/polypeptides/proteins of the present invention can also result from a nonsense mutation, i.e., a SNP that creates a premature stop codon, a SNP that generates a read-through mutation by abolishing a stop codon, or due to any SNP disclosed by the present invention that otherwise alters the structure, function/activity, or expression of a protein, such as a SNP in a regulatory region (e.g., a promoter or enhancer) or a SNP that leads to alternative or defective splicing, such as a SNP in an intron or a SNP at an exon/intron boundary. As used herein, the terms "polypeptide", "peptide", and "protein" are used interchangeably.

For all embodiments, the terms "individual" and "host" are used interchangably, and are not limited to humans. According to an aspect of the present invention, the "individual" may be any vertebrate, including mammals such as primates and including humans, dogs, cats, cows, goats, pigs, sheep, and monkeys. Thus, the disclosed invention may be applicable to treatment of animals through, for example, animal water, animal feed, animal pharmaceuticals, and the like. According to an aspect of the present invention, the individual may be healthy or suffering from a disease. In general, however, methods of the present invention can be effectively used if applied to a human who suffers from an auto-immunity disease or a disease caused by a pathogenic microorganism and a type of a certain nucleic acid sequence in the individual.

The term "altered" may be used herein to encompass either an increased or a decreased risk/likelihood.

The term "specific disease," "disease" or "disorder" used herein encompasses auto antibody diseases as well as diseases associated with a pathogenic microorganism, such as for example, a virus, bacterium, yeast or mycoplasma as well as oncological diseases. However, the disease is not particularly limited.

The term "practitioner" or "medical practitioner" used herein includes any person who engages in medicine or related medical arts as a profession, including the medical, biotechnology or pharmaceutical industry.

DETAILED DESCRIPTION OF THE INVENTION

The present invention provides methods of determining if an individual is likely to develop immune tolerance by detecting the altered expression (either higher or lower expression) or unique expression of nucleic acid sequences, as well as the gene sequence in the individual, even if they are not expressed or only transiently expressed. As such, some embodiments provide methods to determine if an individual that has the ability to develop immune tolerance has a differential and unique expression of known and unknown nucleic acid sequence from those individuals who do not have the ability to develop immune tolerance. In some embodiments, the nucleic acid sequences are SNPs.

The present invention also provides nucleic acid sequences, methods and reagents for detecting the nucleic acid sequences, uses of nucleic acid sequences in kits or assays for use in advance of inducing immune tolerance.

The invention contemplates use of nucleic acid sequences that are associated with either an increased risk of having or developing immune tolerance, or a decreased risk of having or developing immune tolerance. The presence of certain nucleic acid sequences (or their mRNA or protein encoded products) can be assayed to determine whether an individual possesses a nucleic acid sequences that is indicative of an increased risk of having or developing immune tolerance or a decreased risk of having or developing immune tolerance.

Similarly, the nucleic acid sequences of the present invention can be associated with either an increased or decreased likelihood of responding to a particular treatment or antigen, or an increased or decreased likelihood of developing immune tolerance to the particular treatment or antigen.

In some embodiments, the nucleic acid sequences are SNPs. Such nucleic acid variation can be assayed in a number of different methods that are well known to those of skill in the art, including PCR, RFLP, hybridization and direct sequencing.

Determination of Nucleic Acid Presence/Absence in Individuals Susceptible to Immune Tolerance One embodiment is to a method to determine nucleic acid sequences that are present or absent in an individual who is susceptible to immune tolerance development, comprising screening for at least one nucleic acid sequence, as show in FIG. 1. In this method, the medical practitioner first administers an oral antigen to a patient to induce immune tolerance (101).

Antigens suitable for use in the present invention include, but are not limited to, synthetic or naturally derived proteins and peptides, and particularly those which by themselves require high doses to induce oral tolerance; carbohydrates including, but not limited to, polysaccharides and lipopolysaccharides; and antigens isolated from biological sources such as, for example, those associated with or responsible for the induction of auto-immune diseases, clinical (allergic) hypersensitivities, and allograft rejection and subunits or extracts therefrom; or any combination thereof.

Further, the antigens may be any associated with or responsible for the induction of auto-immune diseases, clinical (allergic) hypersensitivities, and allograft rejection, and subunits or extracts therefrom; or recombinantly generated whole proteins, subunits or fragments thereof; or any combination thereof.

The antigen administered may include, but is not limited to, all of the antigens of Table 1, to treat the associated diseases. The associated diseases or disorders listed in the Table 1 are meant to be examples and are in no way inclusive. In one specific embodiment, the at least one antigen is a collagen selected from the group of: I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, and mixtures thereof. The collagen may also be a fragment thereof. For instance, the collagen may be one or more fragments produced by CNBr cleavage of α1(I), which yields eight CB fragments: CB0, CB1, CB2, CB4, CB5, CB8, CB3, CB7 and CB6. The collagen may be one or more fragments produced by cCNBr cleavage of α2(I), which yields six CB fragments: CB1, CB0, CB4, CB2, CB3 and CB5.

Further, in one embodiment, the disease is a sclerotic disease. In another embodiment, the disease is multiple sclerosis.

Table 1 shows multiple embodiments of the invention. For instance, in one embodiment, collagen is the antigen used to induce immune tolerance to the disease idiopathic pulmonary fibrosis. In another embodiment, α-enolase is an antigen used to induce immune tolerance for the disease asthma.

Furthermore, the individual dose size, number of doses, frequency of dose administration, and mode of administration may vary. Determination of such protocols can be accomplished by those skilled in the art. A suitable single dose is a dose that is capable of altering a biological response in an animal when administered one or more times over a suitable time period (e.g., from minutes to days over weeks). Preferably, a dose comprises from about 1 ng of the antigen per kilogram of body weight (ng/kg) to about 1 gram of antigen per kilogram of body weight (gm/kg), more preferably 100 ng/kg to about 100 milligrams/kilogram (mg/kg), and even more preferably from about 10 microgram of the antigen per kilogram body weight (µg/kg) to about 10 mg/kg.

Alternatively, the dose of antigen may not be determined upon the body weight of the patient. In this embodiment, the dose may be at least 1 ng/day of antigen. Preferably, the dose ranges from 10 µg/day of antigen to 5000 µg/day. In another embodiment, the dose ranges from 10 µg/day of antigen to 500 µg/day. In another embodiment, the dose ranges from 30 µg/day of antigen to 200 µg/day.

In one alternate embodiment, the dose of antigen is below the threshold required for stimulation of an immune response. In another embodiment, the dose of antigen is above the threshold, thereby stimulating an immune response.

Modes of administration can include, but are not limited to, aerosolized, subcutaneous, rectally, intradermal, intravenous, nasal, oral, transdermal and intramuscular routes. In one preferred embodiment, the antigen is given orally. In another preferred embodiment, the antigen is given intravenously or sublingually.

Furthermore, the antigen can be combined with other components such as a pharmaceutically acceptable excipient and/or a carrier, prior to administration to the individual. The other components will depend upon the mode of administration, storage needs, and the like.

Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, or dextran. Excipients can also contain minor amounts of additives, such as substances that enhance isotonicity and chemical stability. Examples of buffers include, but are not limited to, phosphate buffer, bicarbonate buffer and Tris buffer, while examples of preservatives include, but are not limited to, thimerosal, m- or o-cresol, formalin and benzyl alcohol.

Standard formulations can either be liquid injectables or solids that can be taken up in a suitable liquid as a suspension or solution for injection. Carriers are typically compounds that increase the half-life of an antigen in the treated individual. Suitable carriers include, but are not limited to, polymeric controlled release vehicles, biodegradable implants, liposomes, bacteria, viruses, oils, esters, and glycols. Preferred controlled release formulations are capable of slowly releasing the antigen of the present invention into an individual. Suitable controlled release vehicles include, but are not limited to, biocompatible polymers, other polymeric matrices, capsules, microcapsules, microparticles, bolus preparations, osmotic pumps, diffusion devices, liposomes, liposphere, and transdermal delivery systems. Other controlled release vehicles of the present invention include liquids that, upon administration to an individual, form a solid or a gel in situ. Preferred controlled release vehicles are biodegradable (i.e., bioerodible).

A biological sample, also referred to as a "sample", is taken from the individual for use in determining the individual's immune response (102). Such sample preparation components can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue specimens. The frequency of taking samples, and its use, will vary based on such factors as the scoring method, assay format, nature of the detection method, and the specific tissues, cells or extracts used as the test sample to be assayed. Methods of preparing nucleic acids, proteins, and cell extracts from the biological sample are well known in the art and can be readily adapted to obtain a sample that is compatible with the system utilized.

From the biological sample, the individual immune system response to the antigen is determined, and the individuals are scored based upon their response (103). The method of scoring is dependent upon the practitioner, and includes any methods that separate patients based upon their immune response to the antigen. For instance, the patient may be scored based on antigen specific and antigen non-specific assays. Antigen specific assays measure the response of T and B cells to specific antigens, whereas antigen non-specific assays determine the phenotype of surface markers or functional state of cells for patterns associated with a particular clinical status.

Specifically, the practitioner may use any means convenient to determine the immune system response, including but not limited to, use of an enzyme-linked immunoabsorbent assay (ELISA), ELISA/ACT® Lymphocyte Response Assay (LRA), in vitro measurement of antibody production, mixed leukocyte reaction, cytotoxic T lymphocyte assay, flow cytometry, Western blots, limiting dilution assay, mass spectroscopy, immunoprecipitation and immunofluorescence.

For instance, in one embodiment, an ELISPOT assay is used to determine the individual immune response. Typically, an ELISPOT assay includes incubating immune cells in plates coated with a capture antibody against a cytokine of interest. Cytokines released by the cell membrane are then captured by the capture antibody during the incubation period. The cells are removed and the bound cytokine is detected using a labeling system, such as for example, a labeled secondary antibody against a different epitope of the same cytokine. This assay results in a cytokine footprint of a single cell.

In another embodiment, a transvivo DTH assay is used to determine individual immune response. In this assay, cells from the individual are injected into the footpads of immune-deficient mice together with the antigen. The index of reactivity of T cells to the antigens is then measured by quantification of resultant swelling in the footpad.

In another embodiment, a tetramer assay is used. Here, the frequency of T cells is measured by their binding to specific peptide-MHC complexes using flow cytometry.

In an alternate embodiment, a CFSE assay measures the proliferation of T cells by dilution of a CFSE dye in the dividing cells. This assay may include use of flow cytometry.

In yet another embodiment, intracellular staining of the T cells can be used to determine the frequency of cytokine-producing T cells by, for example, flow cytometry.

In yet another embodiment, the patients are scored based upon the respective levels and/or changes in IFN-γ production before, during and/or after receiving the antigen. Alternatively, other cytokines may be measured to determine individual scores. For instance, levels of IL-10 in α1(I)- and α2(I)-stimulated PBMC culture supernatants and/or sIL-2R may be used to score a patient.

Other means to determine the immune system response may include characterization of the TCR repertoire. This assay may include use of quantitative PCR, gel electrophoresis and DNA sequencing to determine the proporation of T cells that use the Vβ chains to determine the CFR3 length distribution along the Vβ gene product.

Another means to determine immune system response may include T cell responses to polyclonal, non-antigen-specific stimulation. Here, the whole blood is stimulated with phytohaemagglutinin for a period of time, CD4+ cells are then isolated, and the extent of early CD4+ cell activation is measured by the synthesis and accumulation of intracellular ATP measured after cell lysis.

Other means to determine the immune system response may include, but is not limited to, detection of the presence of nucleic acids. Several methods of detecting nucleic acids are available including PCR, LCR and hybridization techniques. Hybridization techniques involve detecting the hybridization of two or more nucleic acid molecules, where detection is achieved in a variety of ways, including labeling the nucleic acid molecules and observing the signal generated from such a label. Hybridization techniques may include any of the following: Northern and Southern blotting, cycling probe reaction, branched DNA, Invader™ Assay, and Hybrid Capture. Hybridization techniques may also be used to identify a specific sequence of nucleic acid present in a sample by using microarrays (or "bioarrays") of known nucleic acid sequences to probe a sample. Bioarray technologies generally use known single stranded nucleic acid, where each unique short chain is attached in a specific known location and then adding the sample nucleic acid and allowing sequences present in the sample to hybridize to the immobilized strands. Detection of this hybridization is then carried out by labeling, typically end labeling, of the fragments of the sample to be detected prior to the hybridization. Further, hybridization may be determined by use of a fluorescent in situ hybridization technique.

Furthermore, in one embodiment, a proteomics approach may be used. Here, protein microarrays or mass spectrometry may be used to determine the presence and quantification of protein fragments present in an individual's sample. In addition, by analyzing more than one protein, the practitioner can determine the immune response by the unique patterns of protein expression in the individual.

To score the patients based on immune system response, the practitioner may measure compare the immune response before, during and/or after receiving the antigen. The determination of when the immune response is measured, and what method is used, is based upon the practitioner needs. Further, it is contemplated that the practitioner may further take into consideration other physiological factors of the individual, such as other cytokines, percentage of T cell, NK cell, B cell, dendritic cell, monocyte, subpopulations, oxidative radicals, connective tissue growth factor, nitric oxide, thymic morphology determined by imaging techniques, patient height, nutritional status, weight, health, thymic function determined by immunologic assays, diet, gender, age, vitamin A levels, zinc levels, and environmental considerations to assist in scoring the patient's immune response. Patients' genomic backgrounds, such as mutations in other genes or genome regions, races and gender differences, may also be considered.

Once the individual is scored based on antigen response, the practitioner will analyze the genotype of the individuals to determine whether an individual has or lacks one or more nucleic acid sequences, thereby altering levels or patterns of gene expression (104). The genotype is later used to correlate the presence or absence of the one or more nucleic acids with the immune response score of step (103).

The practitioner may either examine specific known nucleic acids of interest or examine part or whole of the entire genome to look for the presence or absence of differential or unique nucleic acids or nucleic acid patterns, and correlate the one or more nucleic acids presence/absence with the individual's immune response score. Nucleic acids of particular interest include those known to affect the concentration of mRNA or protein in a sample, nucleic acids known to affect the kinetics of nucleic acid and/or protein expression, nucleic acids that affect the rate of nucleic acid and/or protein decomposition, and nucleic acids that affect protein stability profile, Km, or Vmax.

Further, the practitioner may either use part of the biological sample of step (102) to analyze for the nucleic acid, or the practitioner may take another biological sample from the individual for analysis. The nucleic acid may be purified or isolated from the sample by any means convenient to the practitioner, but such isolation may not be necessary in certain forms of detection.

In one preferred embodiment, the practitioner will analyze the genotype of the individuals to determine which allele(s) is/are present at any given genetic region of interest by methods well known in the art. The neighboring sequence can be used to design nucleic acid detection reagents such as oligonucleotide probes, which may optionally be implemented in a kit format.

Common genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA, multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, timeresolved fluorescence detection, fluorescence resonance energy transfer, fluorescence polarization, mass spectrometry, and electrical detection.

Various methods for detecting polymorphisms include, but are not limited to, methods in which protection from cleavage agents is used to detect mismatched bases in RNA/RNA or RNA/DNA, comparison of the electrophoretic mobility of variant and wild type nucleic acid molecules, and assaying the movement of polymorphic or wild-type fragments in polyacrylamide gels containing a gradient of denaturant using denaturing gradient gel electrophoresis. Sequence variations at specific locations can also be assessed by nuclease protection assays such as RNase and SI protection or chemical cleavage methods.

In one embodiment, genotyping is performed using the TaqMan assay, which is also known as the 5' nuclease assay. The TaqMan assay detects the accumulation of a specific amplified product during PCR. The TaqMan assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively, or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Preferred TaqMan primer and probe sequences can readily be determined using the SNP and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the nucleic acids of the present invention are useful in diagnostic assays for stenosis and related pathologies, and can be readily incorporated into a kit format. The present invention also includes modifications of the Taqman assay well known in the art such as the use of Molecular Beacon probes and other variant formats.

Another method for genotyping the nucleic acids of the present invention is the use of two oligonucleotide probes in an OLA. In this method, one probe hybridizes to a segment of a target nucleic acid with its 3' most end aligned with the nucleic acid site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the nucleic acid site. If there is a mismatch, efficient ligation cannot occur. After the reaction, the ligated probes are separated from the target nucleic acid molecule, and detected as indicators of the presence of a nucleic acid sequence. OLA may also be used for performing nucleic acid detection using universal arrays, wherein a zipcode sequence can be introduced into one of the hybridization probes, and the resulting product, or amplified product, hybridized to a universal zip code array. Alternatively OLA may be used where zipcodes are incorporated into OLA probes, and amplified PCR products are determined by electrophoretic or universal zipcode array readout.

Alternatively one may use SNPlex methods and software for multiplexed SNP detection using OLA followed by PCR, wherein zipcodes are incorporated into OLA probes, and amplified PCR products are hybridized with a zipchute reagent, and the identity of the SNP determined from electrophoretic readout of the zipchute. In some embodiments, OLA is carried out prior to PCR (or another method of nucleic acid amplification). In other embodiments, PCR (or another method of nucleic acid amplification) is carried out prior to OLA.

Another method for genotyping is based on mass spectrometry. Mass spectrometry takes advantage of the unique mass of each of the four nucleotides of DNA. Nucleic acids can be unambiguously genotyped by mass spectrometry by measuring the differences in the mass of nucleic acids having alternative nucleic acid alleles. MALDI-TOF (Matrix Assisted Laser Desorption Ionization—Time of Flight) mass spectrometry technology is preferred for extremely precise determinations of molecular mass, such as for SNPs. Numerous approaches to genotype analysis have been developed based on mass spectrometry. Preferred mass spectrometry-based methods of nucleic acid genotyping include primer extension assays, which can also be utilized in combination with other approaches, such as traditional gel-based formats and microarrays.

Typically, the primer extension assay involves designing and annealing a primer to a template PCR amplicon upstream (5') from a target nucleic acid position. A mix of dideoxynucleotide triphosphates (ddNTPs) and/or deoxynucleotide triphosphates (dNTPs) are added to a reaction mixture containing template. For example, in some embodiments this is a SNP-containing nucleic acid molecule which has typically been amplified, such as by PCR. Primer and DNA polymerase may further be added. Extension of the primer terminates at the first position in the template where a nucleotide complementary to one of the ddNTPs in the mix occurs. The primer can be either immediately adjacent (i.e., the nucleotide at the 3' end of the primer hybridizes to the nucleotide next to the target SNP site) or two or more nucleotides removed from the nucleic acid position. If the primer is several nucleotides removed from the target nucleic acid position, the only limitation is that the template sequence between the 3' end of the primer and the nucleic acid position cannot contain a nucleotide of the same type as the one to be detected, or this will cause premature termination of the extension primer.

Alternatively, if all four ddNTPs alone, with no dNTPs, are added to the reaction mixture, the primer will always be extended by only one nucleotide, corresponding to the target SNP position. In this instance, primers are designed to bind one nucleotide upstream from the SNP position (i.e., the nucleotide at the 3' end of the primer hybridizes to the nucleotide that is immediately adjacent to the target SNP site on the 5' side of the target SNP site). Extension by only one nucleotide is preferable, as it minimizes the overall mass of the extended primer, thereby increasing the resolution of mass differences between alternative SNP nucleotides. Furthermore, mass-tagged ddNTPs can be employed in the primer extension reactions in place of unmodified ddNTPs. This increases the mass difference between primers extended with these ddNTPs, thereby providing increased sensitivity and accuracy, and is particularly useful for typing heterozygous base positions. Mass-tagging also alleviates the need for intensive sample-preparation procedures and decreases the necessary resolving power of the mass spectrometer.

The extended primers can then be purified and analyzed by MALDI-TOF mass spectrometry to determine the identity of the nucleotide present at the target SNP position. In one method of analysis, the products from the primer extension reaction are combined with light absorbing crystals that form a matrix. The matrix is then hit with an energy source such as a laser to ionize and desorb the nucleic acid molecules into the gas-phase. The ionized molecules are then ejected into a flight tube and accelerated down the tube towards a detector. The time between the ionization event, such as a laser pulse, and collision of the molecule with the detector is the time of flight of that molecule. The time of flight is precisely correlated with the mass-to-charge ratio (m/z) of the ionized molecule. Ions with smaller m/z travel down the tube faster than ions with larger m/z and therefore the lighter ions reach the detector before the heavier ions. The time-of-flight is then converted into a corresponding, and highly precise, m/z. In this manner, SNPs can be identified based on the slight differences in mass, and the corresponding time of flight differences, inherent in nucleic acid molecules having different nucleotides at a single base position.

Nucleic acids can also be scored by direct DNA sequencing. A variety of automated sequencing procedures can be used, including sequencing by mass spectrometry. The nucleic acid sequences of the present invention enable one of ordinary skill in the art to readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing. Nucleic acid sequences can also be determined by employing a high throughput mutation screening system, such as the SpectruMedix system.

Other methods that can be used to genotype the nucleic acids of the present invention include single-strand conformational polymorphism (SSCP), and denaturing gradient gel electrophoresis (DGGE). SSCP identifies base differences by alteration in electrophoretic migration of single stranded PCR products. Single-stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at nucleic acid positions. DGGE differentiates nucleic acid alleles based on the different sequence-dependent stabilities and melting properties inherent in polymorphic DNA and the corresponding differences in electrophoretic migration patterns in a denaturing gradient gel.

Sequence-specific ribozymes can also be used to score nucleic acids, in particular SNPs, based on the development or loss of a ribozyme cleavage site. Perfectly matched sequences can be distinguished from mismatched sequences by nuclease cleavage digestion assays or by differences in melting temperature. Thus, for example, if the SNP affects a restriction enzyme cleavage site, the SNP can be identified by alterations in restriction enzyme digestion patterns, and the corresponding changes in nucleic acid fragment lengths determined by gel electrophoresis Genotyping can include the steps of, for example, collecting a biological sample from a human subject (e.g., sample of tissues, cells, fluids, secretions, etc.), isolating nucleic acids (e.g., genomic DNA, mRNA or both) from the cells of the sample, contacting the nucleic acids with one or more primers which specifically hybridize to a region of the isolated nucleic acid containing a target nucleic acid region of interest under conditions such that hybridization and amplification of the target nucleic acid region occurs, and determining the nucleotide present at the nucleic acid position of interest, or, in some assays, detecting the presence or absence of an amplification product (assays can be designed so that hybridization and/or amplification will only occur if a particular nucleic acid sequence allele is present or absent). In some assays, the size of the amplification product is detected and compared to the length of a control sample; for example, deletions and insertions can be detected by a change in size of the amplified product compared to a normal genotype.

Furthermore, the nucleic acid, or in particular the SNP, found may then be compared to the nucleic acids of other individuals whom have also received the antigen to induce an immune response. Methods of comparing the identity of two or more sequences may be performed by any reasonable means, including programs available in the Wisconsin Sequence Analysis Package version 9.1 (Genetics Computer Group, Madison, Wis., USA). Other programs such as BESTFIT may be used to find the "local homology" algorithm of Smith and Waterman and finds the best single region of similarity between two sequences. Further, programs such as GAP may be used, which aligns two sequences finding a "maximum similarity." Preferably, % identities and similarities are determined when the two sequences being compared are optimally aligned. Other programs for determining identity and/or similarity between sequences are also known in the art, for instance the BLAST family of programs, available from the National Center for Biotechnology Information (NCB), Bethesda, Md., USA) and FASTA, available as part of the Wisconsin Sequence Analysis Package.

Once the presence or absence or pattern of nucleic acids present in an individual is determined, the immune response score is associated with the nucleic acid results. The practitioner may then determine if one or more nucleic acids, preferably SNPs, are associated with individuals who did or did not respond to the antigen with altered immune tolerance.

It is contemplated that the mechanisms of induction of immune tolerance may vary with different diseases and disorders. For example, the SNP involved with induction of systemic lupus erthematosus may be different from the SNPs involved with other diseases, such as autoimmune encephalopathy. As such, the practitioner may repeat the process of FIG. 1 for each disease and disorder that the practitioner wishes to induce immune tolerance to.

Determination of Treatment Based Upon an Individual's Genotyping

Figure 2:
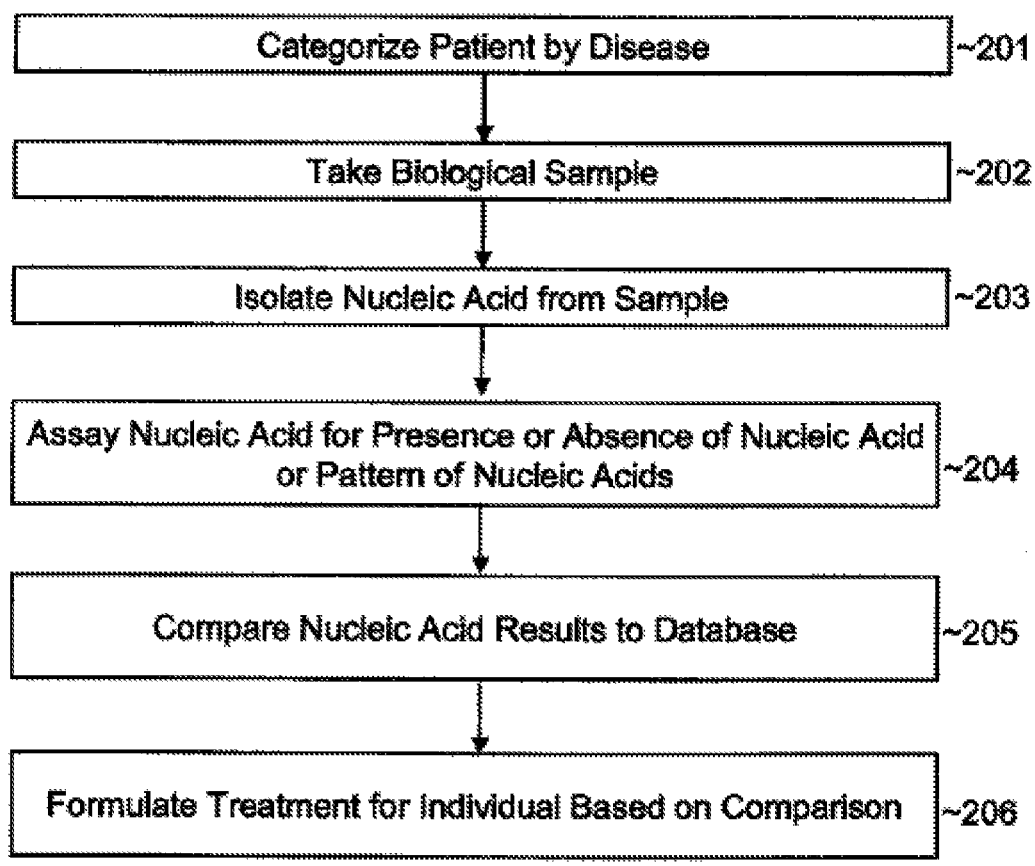
FIG. 2 illustrates a flow chart in accordance with some embodiments of the invention, demonstrating a process of determining an individual's treatment regiment by the presence of absence of one or more nucleic acids.

The method of FIG. 1 is particularly beneficial because it allows the practitioner to determine what nucleic acid sequences, including SNPs, may be involved with induction of immune tolerance. More importantly, once the method of FIG. 1 is complete, the practitioner may simply test a new individual for the nucleic acid sequence or SNP of interest, as outlined in FIG. 2.

First, the practitioner categorizes or diagnoses the patient as having a disease or disorder (201). The categorization or diagnosis may be based on present or past symptoms, medical history, family history, tests such as assays or medical scans, and the like.

Once the practitioner has diagnosed the patient, the practitioner takes a biological sample from the patient (202). The sample may be in any form convenient for the practitioner and patient, including but not limited to, whole blood, blood plasma, urine, tears, semen, saliva, buccal mucosa, interstitial fluid, lymph fluid, meningeal fluid, amniotic fluid, glandular fluid, sputum, feces, perspiration, mucous, vaginal secretion, cerebrospinal fluid, hair, skin, fecal material, wound exudate, wound homogenate, and wound fluid.

The individual's nucleic acid is then isolated from the sample (203). The isolation may occur by any means convenient to the practitioner. For instance, the isolation may occur by first lysing the cell using detergents, enzymatic digestion or physical disruption. The contaminating material is then removed from the nucleic acids by use of, for example, enzymatic digestion, organic solvent extraction, or chromatographic methods. The individual's nucleic acid may be purified and/or concentrated by any means, including precipitation with alcohol, centrifugation and/or dialysis.

The individual's nucleic acid is then assayed for presence or absence of one or more predetermined nucleic acids of interest (204). The one or more predetermined nucleic acids of interest may be any nucleic acid the practitioner believes may be related to immune tolerance to any disease or disorder. Exemplary examples of appropriate diseases or disorders are listed in Table 1.

The determination of whether one or more predetermined nucleic acids of interest are presence or absence, may be done by any mean (205).

In one embodiment, the predetermined nucleic acid of interest is an approximately 50 KB non gene region on chromosome 12, located about 55.5 Mbp from the proximal end of chromosome 12 between 66,603,791 and 66,603,991 bps, where the nucleic acid of interest is either TTTTTTTTTTGTACCTAGTTCTATGGTTACCTT (SEQ ID NO. 1) or TTTTTTTTTTGTACCTGGTTCTATGGTTACCTT (SEQ ID NO. 2). The A/G is the polymorphic site. Thus, AA represents AA homozygous, while AB represents A/G heterozygous and BB represents GG genotype, A→G represents the polymorphism site.

Alternatively, the predetermined nucleic acid of interest may include part of the approximately 265143 by at 5' side of SNP A-1515737. Alternatively, the predetermined nucleic acid of interest may include part of the approximately 231513 by at 3' side of SNP-1515737. Alternatively, the predetermined nucleic acid of interest includes part of all of SEQ. ID. 3 or 4.

In another embodiment, the predetermined nucleic acid of interest is located between 66507155-66507464 on chromosome 12, within the proximity of the marker D12S1503.

In another embodiment, the predetermined nucleic acid of interest is located within the proximity of D12S1676, i.e., part or all of the predetermined nucleic acid of interest is located between 66499298-66499423 on chromosome 12.

In another embodiment, the predetermined nucleic acid of interest is located within the proximity of D12S335, i.e., part or all of the predetermined nucleic acid of interest is located between 66415802-66416056 on chromosome 12.

In another embodiment, the predetermined nucleic acid of interest is located within the proximity of D12S102, i.e., part or all of the predetermined nucleic acid of interest is located between 66781046-66781298 on chromosome 12.

In another embodiment, the predetermined nucleic acid of interest is located within the proximity of D12S1506, i.e., part or all of the predetermined nucleic acid of interest is located between 66785380-66785614 on chromosome 12.

In another embodiment, the predetermined nucleic acid of interest is SNP_A-1508498 (TSC51977), with the polymorphism of C or T. In another embodiment, the predetermined nucleic acid of interest is SNP_A-1512645 (TSC1720860) with the polymorphism of C or T. In another embodiment, the predetermined nucleic acid of interest is SNP_A-1512719 (TSC1720861) with the polymorphism of C or T. In another embodiment, the predetermined nucleic acid of interest is SNP_A-1515330 (TSC1244733) with the polymorphism of C or T. In another embodiment, the predetermined nucleic acid of interest is SNP_A-1518829 (TSC51583) with the polymorphism of A or G. In another embodiment, the predetermined nucleic acid of interest is SNP_A-1518878 (TSC51584) with the polymorphism of C or G. Further, in one specific embodiment, the predetermined nucleic acid of interest is located within 30 kbp of SNP_A-1515737. These other markers and transcripts can also be used to determine a patient's ability to have tolerance, especially oral tolerance, induced.

In another embodiment, the predetermined nucleic acid of interest is D12S1503 (SEQ. ID. NO. 5). In another embodiment, the predetermined nucleic acid of interest is D12S1676 (SEQ. ID. NO. 6). In another embodiment, the predetermined nucleic acid of interest is D12S335 (SEQ. ID. NO. 7). In another embodiment, the predetermined nucleic acid of interest is D12S102 (SEQ. ID. NO. 8).

Figure 15:
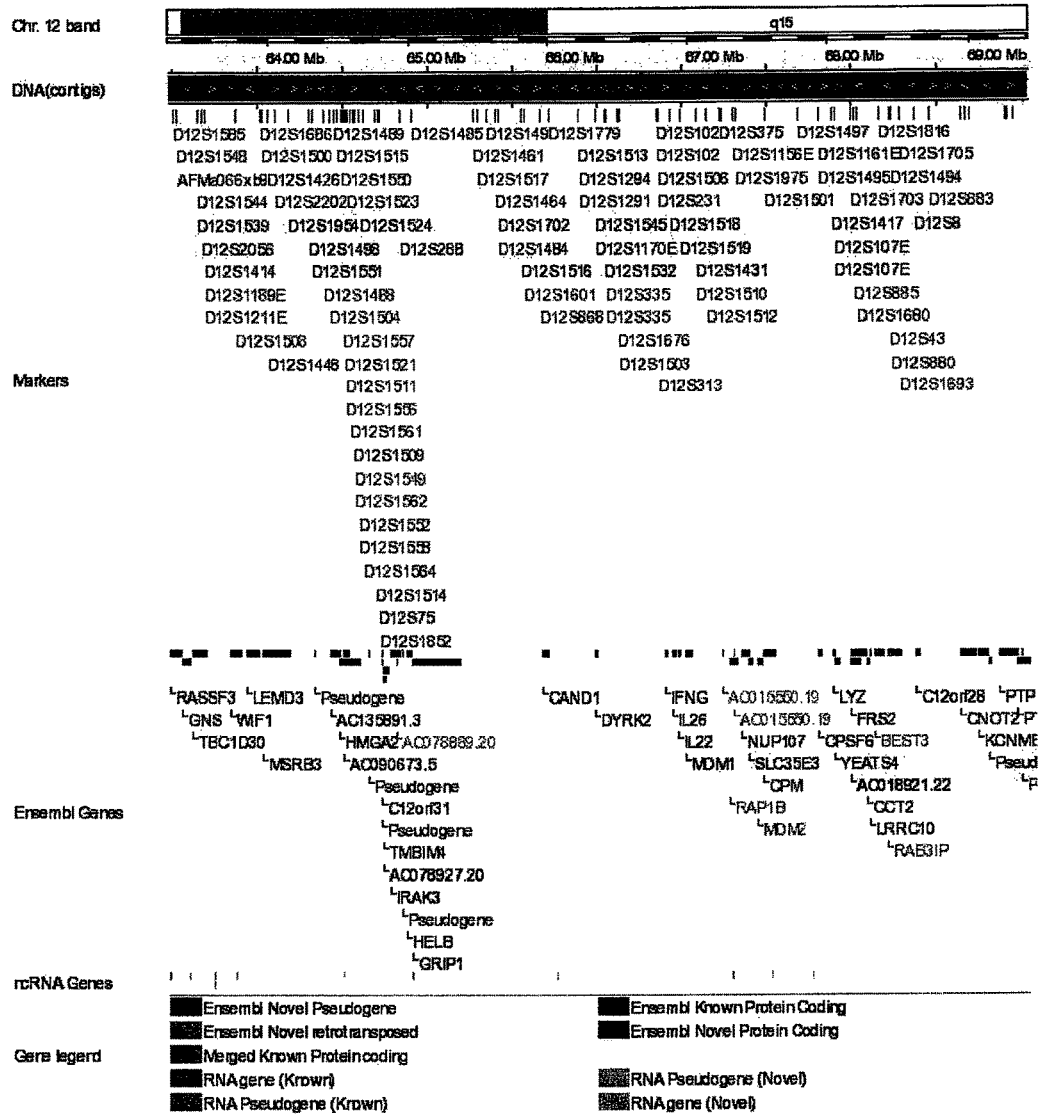
FIG. 15 is a chart showing the markers and genes contain potential SNPs of interest.

In another embodiment, the predetermined nucleic acid of interest is SNP_A-1508498 with a polymorphism of C or T. (SEQ. ID. NO. 9 and 10). In another embodiment, the predetermined nucleic acid of interest is SNP_A-1512645 with a polymorphism of C or T. (SEQ. ID. NO. 11 or 12). In another embodiment, the predetermined nucleic acid of interest is SNP_A-1512719 with a polymorphism of C or T. (SEQ. ID. NO. 13 or 14). In another embodiment, the predetermined nucleic acid of interest is SNP_A-1515330 with a polymorphism of C or T. (SEQ. ID. NO. 15 or 16). In another embodiment, the predetermined nucleic acid of interest is SNP_A-1518829 with a polymorphism of A or G. (SEQ. ID. NO. 17 or 18). In another embodiment, the predetermined nucleic acid of interest is SNP_A-1518878 with a polymorphism of C or G. (SEQ. ID. NO. 19 or 20). The predetermined nucleic acid of interest may also be any marker or gene between 63.3 mbp and 69.4 mbp on human chromosome 12. See, e.g., FIG. 15.

In one embodiment, the practitioner uses visual confirmation of the presence or absence of particular variants of the nucleic acid.

In another embodiment, the method provides a computer based system with one or more algorithms to determine the presence and/or absence of one or more predetermined nucleic acids of interest and, if present, quantifies the amount of one or more predetermined nucleic acids of interest present in the individual's nucleic acid.

In one preferred embodiment, the predetermined nucleic acids of interest are one or more SNPs. Further, the computer based system may comprise information about observed SNP alleles, alternative codons, populations, allele frequencies, SNP types, and/or affected proteins and the like.

The computer based system includes at least one of the following: hardware means, software means, and data storage means used to analyze any information of the present invention. The minimum hardware means of the computer-based systems of the present invention typically comprises a central processing unit (CPU), input means, output means, and data storage means. A skilled artisan can readily appreciate that any one of the currently available computer-based systems are suitable for use in the present invention. Such a system can be changed into a system of the present invention by utilizing information provided on the CD-R, or a subset thereof, without any experimentation.

As stated above, the computer-based systems of the present invention comprise a data storage means having stored therein information and the necessary hardware means and software means for supporting and implementing a search means. The search means of the computer-based system includes one or more software programs or algorithms that are implemented on the computer-based system to identify or analyze nucleic acid sequences, including SNPs in a target sequence, based on nucleic acid information stored within the data storage means. Search means can be used to determine the presence or absence of a nucleic acid sequence, and/or which nucleotide is present at a particular SNP position in a nucleic acid sequence.

In one application of this embodiment, the practitioner may provide the computer-based system with information regarding nucleic acids of interests on a computer readable medium. Computer readable medium is any medium that can be read and accessed directly by a computer, including but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleic acid sequence information of the present invention on computer readable medium. For example, the sequence information can be represented in a word processing text file, formatted in commercially-available software such as WordPerfect and Microsoft Word, represented in the form of an ASCII file, or stored in a database application, such as OB2, Sybase, Oracle, or the like. A skilled artisan can readily adapt any number of data processor structuring formats (e.g., text file or database) in order to obtain computer readable medium having recorded thereon the nucleic acid sequence information of the present invention.

By providing the nucleic acid sequences, including SNPs, of the present invention in computer readable form, a practitioner can routinely access the nucleic acid sequence information for a variety of purposes. Computer software is publicly available which allows a skilled artisan to access sequence information provided in a computer readable medium. Examples of publicly available computer software include BLAST and BLAZE search algorithms.

The present invention further provides systems, particularly computer-based systems, which contain the nucleic acid sequence information described herein. Such systems may be designed to store and/or analyze information on, for example, a large number of SNP positions, or information on genotypes, including SNP genotypes, from a large number of individuals. The nucleic acid sequence information of the present invention represents a valuable information source. The nucleic acid sequence information of the present invention stored/analyzed in a computer-based system may be used for such computer-intensive applications as determining or analyzing nucleic acid allele frequencies in a population, mapping disease genes, genotype-phenotype association studies, grouping SNPs into haplotypes, correlating SNP haplotypes with response to particular drugs, or for various other bioinformatic, pharmacogenomic, drug development, or human identification/forensic applications.

A treatment for the individual is then formulated based on the presence and/or absence of one or more predetermined nucleic acids of interest (206). The treatment may include anything within the means of the practitioner, including a determination of likelihood of inducing immune tolerance can be induced, if so then the type of antigen, dose, method of administration, regiment of treatment, and the like.

The inventors have also discovered that non-steroidal anti-inflammatory drugs (NSAIDS) can interfere with the generation of immune tolerance. Thus, in one alternate embodiment, the practitioner can modulate the creation of immune tolerance by either having the individual desiring treatment stop using NSAIDS or administering pharmaceuticals to reverse the NSAID inhibition of immune tolerance, such as, for example, misoprostol.

Further, in one preferred embodiment, the methods of the instant invention may be used to treat idiopathic pulmonary fibrosis ("IPF"). IPF is a lethal, chronic, progressive, interstitial lung disease in which normal lung tissue is gradually replaced by fibrotic tissue, or an abnormal and excessive amount of fibrotic tissue is deposited in the pulmonary interstitium. This may be described as a scarring of the lung. About 60% of IPF patients have an antigen-specific autoimmune reaction to Type V collagen. Without wishing to be bound to a particular mechanism or theory, it is believed that the immune systems of such patients attack the Type V collagen of the lungs, thereby causing fibrosis.

IPF patients having an autoimmune reaction to Type V collagen would benefit if the immune response attacking the Type V collagen of the lungs could be halted or lessened. This immune response could be halted or lessened by induction of immune tolerance to Type V collagen using the methods of the present invention. Tolerance could be induced by repeated administration of collagen antigens, preferably Type V collagen antigens, according to the methods of the present invention.

Administration of collagen or collagen antigens, preferably Type V collagen or antigens thereof, will be most effective in treating IPF patients who have an antigen-specific autoimmune reaction to Type V collagen. Thus, a test for identifying such patients is desirable.

Using the methods of the present invention, an association study may be performed to determine whether IPF patients having an antigen-specific autoimmune reaction to Type V collagen carry one or more SNPs—or other nucleic acid sequences linked in some manner to the SNPs—that is not found in IPF patients who do not have an antigen-specific autoimmune reaction to Type V collagen. The presence of the one or more SNPs or linked nucleic acid sequences associated with an antigen-specific autoimmune reaction to Type V collagen can then be used to identify patients most likely to benefit from administration of collagen or collagen antigens, preferably Type V collagen or antigens thereof. Autoimmune reactions to Type V collagen are also believed to contribute to rejection of lung transplants. Accordingly, SNP(s) and/or linked nucleic acid sequences found to be associated with an antigen-specific autoimmune reaction to Type V collagen may also be used to assess a patient's propensity to successfully undergo lung or other transplants.

Use of Individual Genotype to Determine Whether to Induce Immune Tolerance

The invention may also be used by the practitioner to determine the regiment of treatment for the individual. That is, based on individual-specific information, the invention may recommend to the practitioner treatment regiments, such as whether to induce immune tolerance, type of antigen, dose, method of administration, regiment of treatment, and the like. The recommendation of treatment regiments may not only be a function of the disease or disorder the individual has, but also a function of the individual characteristics.

Figure 3:
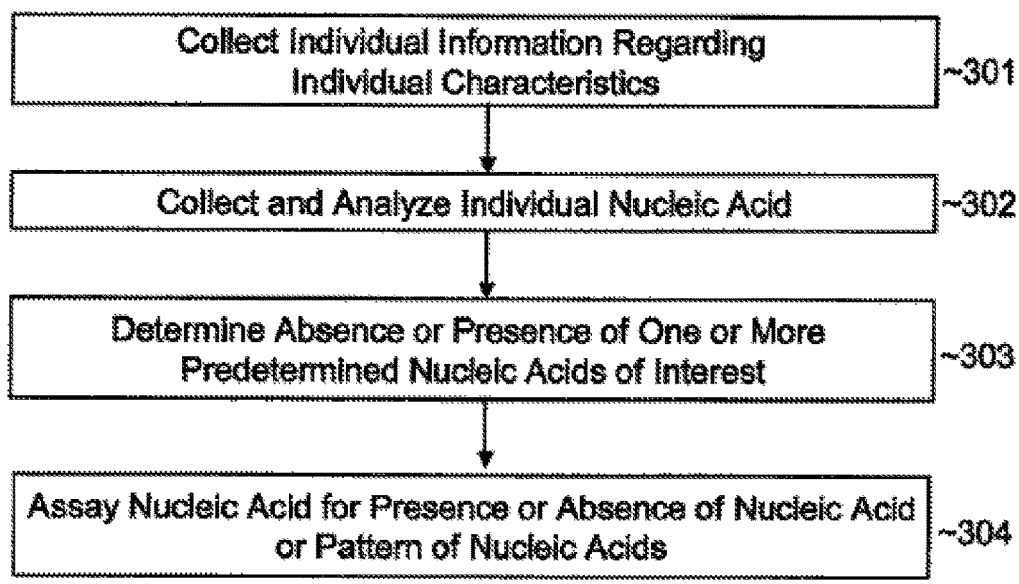
FIG. 3 illustrates a flow chart in accordance with some embodiments of the invention, demonstrating a process of determining an individual's treatment regiment by the presence of absence of one or more nucleic acids.

In this embodiment, the method of which is located in FIG. 3, the individual characteristics are first placed into one or more databases (301). The individual characteristic information may be received by any means, including using an integrated consultation process with one or more practitioners, a questionnaire filled out by the individual, an electronic database, a diagnostic or an expert panel measurement tool, client summary report, and an outcomes measurement report. Further, the individual characteristic information may be received by one or more of a network, oral communication, visual communication, written communication, physical data carrier, and/or any other means capable of conveying information.

Individual characteristics may include, but are not limited to, age, sex, height, weight, individual medical history, family medical history, ethnicity, allergy information, lifestyle information, and the like.

The individual's nucleic acids are then collected and analyzed (302). The method of collecting the individual nucleic acid may be any contemplated by the practitioner, including those mentioned within the instant specification.

The presence or absence of one or more predetermined nucleic acids of interest is then determined (303). Here, the determination which nucleic acids would be examined, i.e., the predetermined nucleic acids of interest, may be determined either individually by the practitioner. Alternatively, the determination includes accessing a database containing information reflecting the relationship between the current disease or diagnosis of the individual, or what the practitioner believes the current disease or diagnosis to be, and the nucleic acids of interest associated with the disease or diagnosis.

In some embodiments, the one or more databases of the current invention are local to the practitioner's location. In other embodiments, the one or more databases are remote, dynamic databases. Generally, a dynamic database is one in which the data within may be easily changed or updated. For instance, one can use a software system to access information from a dynamic database via a network and upload information from the database to the software system. If the information stored in the database changes, the software system connected to the database will also change accordingly and automatically without human intervention. The software system may update the individual's information in the dynamic database on any time bases, including, but not limited to, an event driven, minute-by-minute, hourly, daily or weekly basis.

Based upon the results of step (303), i.e., the presence or absence of one or more predetermined nucleic acids of interest, the treatment of the individual may be determined. In one embodiment, the practitioner relies upon his expertise in the medical field to determine the treatment regiment. In another embodiment, a software system stored in one or more databases recommends a treatment regiment. The recommended treatment regiment may include, but is not limited to, whether to induce immune tolerance, type of antigen, dose, method of administration, regiment of treatment, over the counter or prescription medication, lifestyle changes, and the like.

The recommendation of treatment regiments may not only be a function of the disease or disorder the individual has, but also a function of the individual characteristics. As such, the one or more databases may allow a software system to input more information about the individual, the disease or disorder to be treated, the outcome of the treatment, and other compatible information. It is contemplated that the information for multiple individuals may be pooled together, thus as the amount of data for one or more parameters increases, the algorithm in the software system becomes more robust and accurate at calculating what treatment/procedure best suits the individual's set of criteria. Further, the database may further include a warehouse of "Best Practices," that is, specific treatment protocols judged optimal by a panel of medical experts.

These embodiments allow the practitioner to better tailor the individual's treatment and avoid unnecessary cost and time of unnecessary treatments.

Determination of Nucleic Acids Associated with Immune Tolerance

Figure 4:
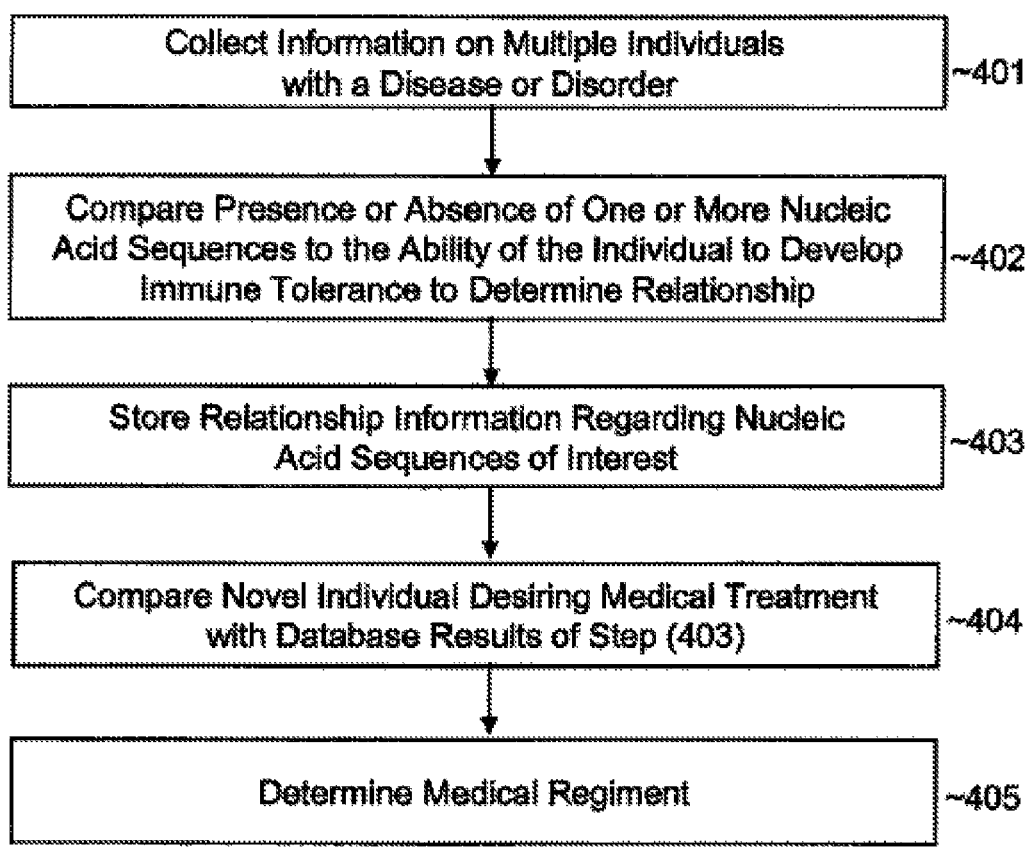
FIG. 4 illustrates a flow chart in accordance with some embodiments of the invention, demonstrating a process of determining an individual's treatment regiment by the presence of absence of one or more nucleic acids.

The determination of which nucleic acids are the predetermined nucleic acids of interest may be determined by the method of FIG. 4. First, information on multiple individuals with a disease or disorder is collected and saved in one or more databases (401). The information includes at least the disease or disorder of the individuals, the ability of the individual to develop immune tolerance after administration of antigens, and the nucleic acid information of the individual. Preferably, the nucleic acid information is the presence or absence of one or more SNPs.

The presence of absence of one or more SNPs and the ability of the individual to develop immune tolerance is compared to determine the increased (or decreased) occurrence of the nucleic acid in a specific disease or disorder condition (402). The comparison of the SNPs and ability to develop immune tolerance may be accomplished by using a mathematical algorithm.

Once a statistically significant association is established between one or more SNPs and ability to induce immune tolerance, then the region around the SNP can optionally be thoroughly screened to identify the causative genetic locus/sequence(s) (e.g., causative SNP/mutation, gene, regulatory, region, etc.) that influences the ability to induce immune tolerance.

In addition, an association study of a SNP and a specific disease or disorder may be performed, to determine the presence or frequency of the SNP allele in biological samples from individuals with the disorder or disease of interest and comparing the information to that of controls (i.e., individuals who do not have the disorder; controls may be also referred to as "healthy" or "normal" individuals) who are preferably of similar age and race. The patients and controls should be as alike as possible in physical characteristics, and a pool of individuals with well-characterized phenotypes is extremely desirable. Further, association studies may also be conducted within the general population and are not limited to studies performed on related individuals in affected families (linkage studies).

The information on the one or more SNPs is then stored in one or more databases, along with information regarding its presence or absence in individuals with the ability to induce immune tolerance (403).

The nucleic acid of individuals who desire treatment for a disease or disorder is then collected and analyzed to find if the individual has the one or more SNPs that are statistically significant associated with the ability of other individuals to induce immune tolerance (404). The medical practitioner alone, or with the assistance of a software system comprising one or more databases, may then determine what medical regiments are feasible, and the parameters of those medical treatments.

Figure 5:
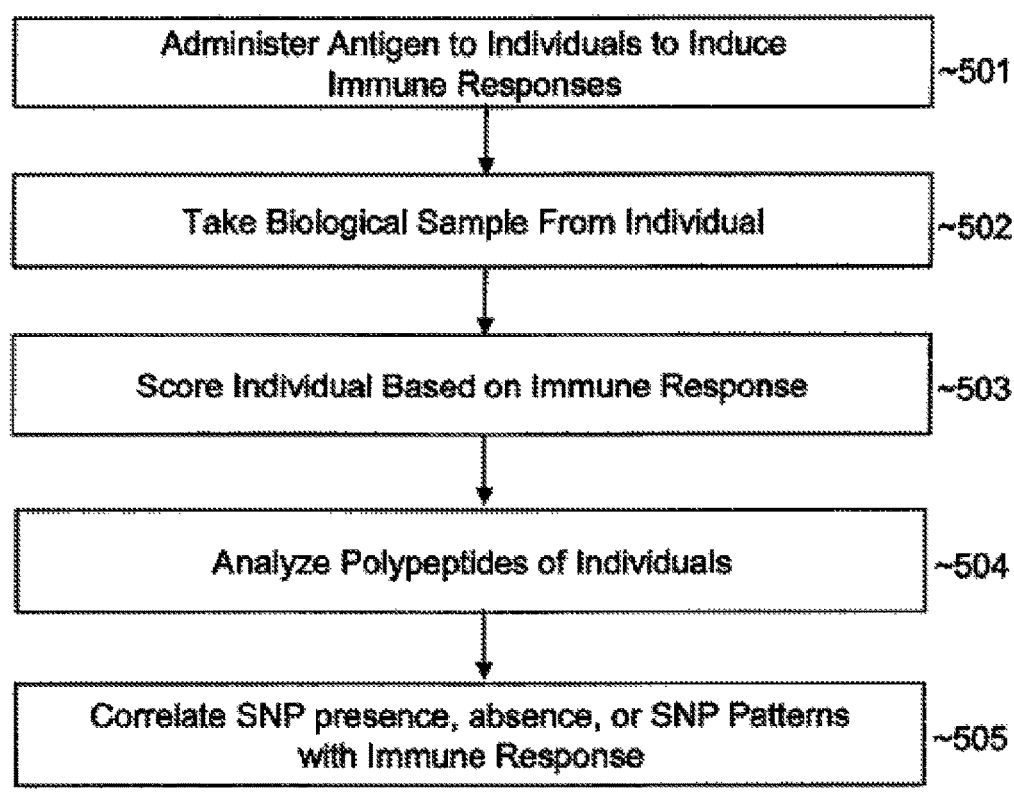
FIG. 5 illustrates a flow chart in accordance with some embodiments of the invention, demonstrating a process of determining an individual's treatment regiment by the presence of absence of one or more polypeptides.

Determination of Altered Polypeptide Presentation in Individuals Susceptible to Immune Tolerance In another embodiment, a method is first used to determining polypeptides that are present or absent in an individual who is susceptible to immune tolerance development, comprising screening for at least one polypeptide, as show in FIG. 5. In this method, the medical practitioner first administers an oral antigen to a patient to induce immune tolerance (501).

Antigens suitable for use in the present invention include those previously discussed, and may include any associated with or responsible for the induction of auto-immune diseases, clinical (allergic) hypersensitivities, and allograft rejection, and subunits or extracts therefrom; or recombinantly generated whole proteins, subunits or fragments thereof; or any combination thereof. Furthermore, the antigen may include, but is not limited to, all of the antigens of Table 1, to treat the associated diseases. The antigen may further be combined with other components such as a pharmaceutically acceptable excipient and/or a carrier, prior to administration to the individual.

The individual dose size, number of doses, frequency of dose administration, and mode of administration may vary be determined by those skilled in the art. Suitable doses of antigen are those previously discussed. Further, the modes of administration can include, but are not limited to, aerosolized, subcutaneous, rectally, intradermal, intravenous, nasal, oral, transdermal and intramuscular routes.

A biological sample is taken from the individual for use in determining the individual's immune response (502), whereby the individual immune system response to the antigen is scored based upon their response (503).

The method to determine the individual immune response may include any method previously discussed, including but not limited to, use of an enzyme-linked immunoabsorbent assay (ELISA), ELISA/ACT® Lymphocyte Response Assay (LRA), in vitro measurement of antibody production, mixed leukocyte reaction, cytotoxic T lymphocyte assay, flow cytometry, Western blots, limiting dilution assay, mass spectroscopy, immunoprecipitation, immunofluorescence, ELISPOT, transvivo DTH assay, tetramer assay, CFSE assay, characterization of the TCR repertoire, measuring T cell responses to polyclonal, non-antigen-specific stimulation, detection of the presence of nucleic acids including PCR, LCR, hybridization techniques and proteomics. In addition, in one specific embodiment, the patients are scored based upon the respective levels and/or changes of cytokine production, including IL-17, IL-2 or IFN-γ production before, during and/or after receiving the antigen. Further, levels of T regulatory cells such as Tr1 cells or $CD4^+$, $CD25^+$, $FoxP3^+$, cells can be used to score patient response. Alternatively, other cytokines may be measured to determine individual scores. For instance, levels of IL-10, IL-4, IL-5 or TGF-β1, 2 or 3 in α1(I)- and α2(I)-stimulated PBMC culture supernatants and/or sIL-2R may be used to score a patient.

The method of scoring is dependent upon the practitioner, and includes any methods that separate patients based upon their immune response to the antigen. To score the patients based on immune system response, the practitioner may measure compare the immune response before, during and/or after receiving the antigen. The determination of when the immune response is measured, and what method is used, is based upon the practitioner needs. Further, it is contemplated that the practitioner may further take into consideration other physiological factors of the individual, such as other cytokines, oxidative radicals, connective tissue growth factor, nitric oxide, patient height, weight, health, diet, and environmental considerations to assist in scoring the patient's immune response.

Once the individual is scored based on antigen response, the practitioner will analyze the polypeptides of the individuals to determine whether an individual has one or more polypeptides or variant polypeptides (504).

The practitioner may either examine specific known polypeptides of interest or examine part or whole of the proteins present in the sample to look for the presence or absence of differential or unique polypeptides or polypeptide patterns, and correlate the polypeptides presence/absence with the individual's immune response score.

Polypeptides may be detected by various methods known to one skilled in the art. Before polypeptide detection, the polypeptides within the individual's biological sample may be purified to substantial purity by standard techniques, including but not limited to, selective precipitation with such substances as ammonium sulfate, cold ethanol precipitation, ultrafiltration, column chromatography, immunopurification methods, and the like.

The polypeptides may be detected by use of any method convenient to the practitioner, including, but not limited to sandwich assays and competition or displacement assays. Typically, a sandwich or competition/displacement assays includes a "capture agent" that specifically bind to and often immobilize the analyte (in this case one or more polypeptides in the sample). The capture agent is a moiety that specifically binds to the analyte.

The presence or absence of the polypeptide may be determined by any means convenient to the practitioner, including electrochemical means or use of labels. A label is any composition detectable by spectroscopic, photochemical, biochemical, immunochemical, electrical, optical or chemical means. Useful labels in the present invention include magnetic beads, fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. The label may be coupled directly or indirectly to the desired component of the assay according to methods well known in the art. The antibody may be produced by any of a number of means well known to those of skill in the art and as described above. Further, the label may be on a third moiety that binds to the capture agent/analyte complex, or secondarily binds to a moiety distinct for the capture agent/analyte complex.

Other techniques that may be used to detect and/or quantify the polypeptide includes western blot (immunoblot) analysis, liposome immunoassays (LIA), proteomics such as protein microarrays or mass spectrometry.

The amino acid sequence of the polypeptides of interest found in the individual's sample may be determined, and compared to one or more databases containing polypeptides amino acid sequences that are statistically significant associated with the ability of other individuals to induce immune tolerance (404). The medical practitioner alone, or with the assistance of a software system comprising one or more databases, may then determine what medical regiments are feasible, and the parameters of those medical treatments.

It is recognized that in any of the embodiments described herein, the disease or disorder may be linked to race, ethnicity, or sex. For example, one study found women comprise 78% of diagnosed autoimmune diseases. Further, systemic sclerosis has a sex and race specific prevalence, where women are more likely than men to have the disorder, and African Americans are more likely then Caucasians to have the disorder. As such, the presence or absence of the nucleic acid of interest may be tied to a hormone, the X chromosome, or to enzymes, receptors, or other compounds that have different levels between the sexes and or races.

SNP Detection Kits and Systems

Based on the SNP and associated sequence information disclosed herein, detection reagents can be developed and used to assay any SNP of the present invention individually or in combination, and such detection reagents can be readily incorporated into one of the established kit or system formats which are well known in the art. Kits used in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, etc.). Accordingly, the present invention further provides SNP detection kits and systems, including but not limited to, packaged probe and primer sets (e.g., TaqMan probe/primer sets), arrays/microarrays of nucleic acid molecules, and beads that contain one or more probes, primers, or other detection reagents for detecting one or more SNPs of the present invention. The kits/systems can optionally include various electronic hardware components; for example, arrays ("DNA chips") and microfluidic systems ("lab-on-a-chip" systems) provided by various manufacturers typically comprise hardware components.

Other kits/systems (e.g., probe/primer sets) may not include electronic hardware components, but may be comprised of, for example, one or more SNP detection reagents (along with, optionally, other biochemical reagents) packaged in one or more containers.

In some embodiments, a SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule. A kit may further contain means for determining the amount of a target nucleic acid, and means for comparing the amount with a standard, and can comprise instructions for using the kit to detect the SNP-containing nucleic acid molecule of interest. In one embodiment of the present invention, kits are provided which contain the necessary reagents to carry out one or more assays to detect one or more SNPs disclosed herein. In a preferred embodiment of the present invention, SNP detection kits/systems are in the form of nucleic acid arrays, or compartmentalized kits, including microfluidic/lab-on-a-chip systems.

SNP detection kits/systems may contain, for example, one or more probes, or pairs of probes, that hybridize to a nucleic acid molecule at or near each target SNP position. Multiple pairs of allele-specific probes may be included in the kit/system to simultaneously assay large numbers of SNPs, at least one of which is a SNP of the present invention. In some kits/systems, the allele-specific probes are immobilized to a substrate such as an array or bead. For example, the same substrate can comprise allele-specific probes for detecting at least 1; 10; 100; 1000; 10,000; 100,000 (or any other number in-between) or substantially all of the SNPs shown in Table 1 and/or Table 2.

The terms "arrays", "microarrays", and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. A microarray can be composed of a large number of unique, single-stranded polynucleotides, usually either synthetic antisense polynucleotides or fragments of cDNAs, fixed to a solid support.

Hybridization assays based on polynucleotide arrays rely on the differences in hybridization stability of the probes to perfectly matched and mismatched target sequence variants. For SNP genotyping, it is generally preferable that stringency conditions used in hybridization assays are high enough such that nucleic acid molecules that differ from one another at as little as a single SNP position can be differentiated (e.g., typical SNP hybridization assays are designed so that hybridization will occur only if one particular nucleotide is present at a SNP position, but will not occur if an alternative nucleotide is present at that SNP position). Such high stringency conditions may be preferable when using, for example, nucleic acid arrays of allele-specific probes for SNP detection.

In other embodiments, the arrays are used in conjunction with chemiluminescent detection technology.

A SNP detection kit/system of the present invention may include components that are used to prepare nucleic acids from a test sample for the subsequent amplification and/or detection of a SNP-containing nucleic acid molecule. Such sample preparation components can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue specimens. The test samples used in the above-described methods will vary based on such factors as the assay format, nature of the detection method, and the specific tissues, cells or extracts used as the test sample to be assayed. Methods of preparing nucleic acids, proteins, and cell extracts are well known in the art and can be readily adapted to obtain a sample that is compatible with the system utilized.

Another form of kit contemplated by the present invention is a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other SNP detection reagent for detecting one or more SNPs of the present invention, one or more containers which contain wash reagents (such as phosphate buffered saline, Tris-buffers, etc.), and one or more containers which contain the reagents used to reveal the presence of the bound probe or other SNP detection reagents. The kit can optionally further comprise compartments and/or reagents for, for example, nucleic acid amplification or other enzymatic reactions such as primer extension reactions, hybridization, ligation, electrophoresis (preferably capillary electrophoresis), mass spectrometry, and/or laser-induced fluorescent detection.

Microfluidic devices, which may also be referred to as "lab-on-a-chip" systems, biomedical micro-electro-mechanical systems (bioMEMs), or multicomponent integrated systems, are exemplary kits/systems of the present invention for analyzing SNPs. Such systems miniaturize and compartmentalize processes such as probe/target hybridization, nucleic acid amplification, and capillary electrophoresis reactions in a single functional device. Such microfluidic devices typically utilize detection reagents in at least one aspect of the system, and such detection reagents may be used to detect one or more SNPs of the present invention.

Further, the kits may also include one or more antigens, as described above. As such, the medical professional may first determine if a SNP is present or absent from the patient. Then, the medical professional prepares a regiment, or uses instead a predetermined regiment, to find which antigen, in what dose, by what method of administration, to give the patient. The one or more antigens may be sold with, or sold separate from, the kit.

Given the disclosure in this application along with information well known to those of skill in the art, many SNPs that correlate with the ability or difficulty of generating immune tolerance can be determined. PCR can be preformed on samples where the replicon contains these SNPs or where the replicon is closely linked to them on the genome. Such technology can provide a rapid assay to determine the likelihood of the ability to induce tolerance in a specific individual.

It should be apparent from the foregoing that an invention having significant advantages has been provided. While the invention is shown in only a few of its forms, it is not just limited but is susceptible to various changes and modifications without departing from the spirit thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, etc., as well as individual numbers within that range, for example, 1, 2, 3, 4, 5, and 6. This applies regardless of the breadth of the range.

Example 1

Rheumatoid Arthritis (RA) Patients

120 RA patients on maintenance conventional therapies for their RA were tested for the ability of their peripheral blood mononuclear cells (PBMC) to produce IFNγ when cultured for six days with the autoantigen, purified bovine α1 chain of Collagen II (CII) or α1(II) at 50 µg/u. Culture supernatants were harvested and IFNγ levels determined by ELISA. IFNγ α1(II)

$$S.I. = \frac{IFN_\gamma\ \alpha1(II) - IFN_\gamma\ PBS}{IFN_\gamma\ PBS} - 100.$$

As shown below (Table I), 76 patients had increased by two-fold over their unstimulated or (PBS) cultured PBMC, or a prevalence of 63% RA patients with an immune responses to CII (termed "Responders"). Although there is a high prevalence of RA patients with CII autoimmunity, it is one of several possible antigens apparent during the disease.

TABLE I

PERCENTAGE of RA PATIENTS WITH IMMUNE RESPONSE by CULTURED PBMC to CII*

| Patient | N | % | Mean IFNγ α1(II) SI ± SEM |
|---|---|---|---|
| Responders E | 76 | 63 | 1494 ± 313 |
| Non-Responders | 44 | 37 | 20.6 ± 6.5 |
| Total | 120 | 100 | p = <0.001** |

**Mann-Whitney Rank Sum Test

Example 2

Low Dose Collagen II Induces Tolerance in DBA/1 Lac Mice

Groups of 12 mice were fed oral CII at the doses indicated 8 times over 2 weeks and immunized with 100 µg bovine CII in CFA. After 4 days rest, the mice were then immunized at the base of the tail with 100 µg CII emulsified with complete Freund's adjuvant. The degree of arthritis was assessed by a blinded observer for 8 weeks.

Figure 6:
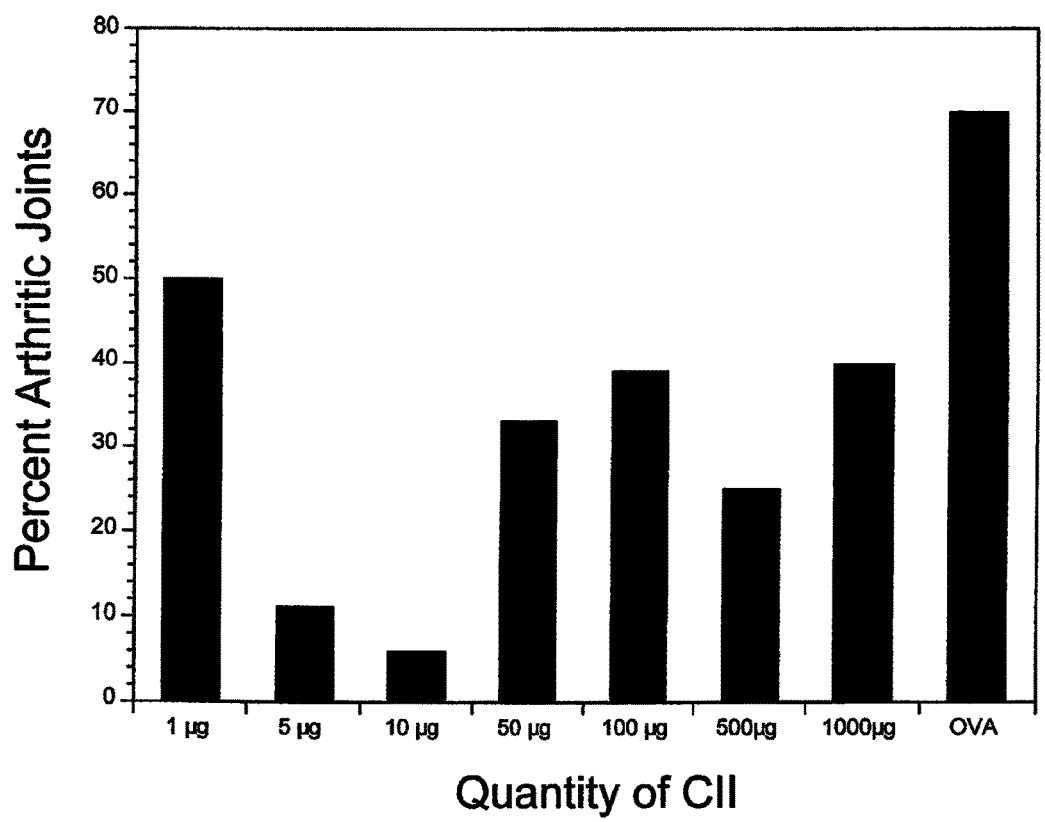
FIG. 6 is a chart showing the percent of arthritic joints correlated with quantity of collagen II given by gavage to mice.

As can be seen in FIG. 6, 10 µg/day oral dose of CII was most effective in reducing the incidence of arthritis with 500 µg/day being also, but less, effective. The percent of mice with grade 3 or 4 arthritis is indicated on the Y-axis. The biphasis response is due to induction of different tolerance mechanisms by low dose vs high dose CII. Low dose CII (10µg) induces regulatory T cells while high dose (500 µg) induces anergy or clonal deletion.

Example 3

NSAID Inhibition of Induction of Immune Tolerance to Collagen II in DBA/1 Mice

To determine whether tolerance induction to orally fed bovine CII in DBA/1 mice would be abrogated by orally fed NSAID, 3 groups of 20-22 DBA/1 mice were fed (by gavage) eight doses (Monday, Tuesday, Thursday, and Friday for 2 weeks) of the following: Placebo (saline) in the a.m. and Placebo (0.1 M HAc) in the p.m.; Placebo (saline)

in the a.m. and 10 µg native bovine CII in the p.m.; or piroxicam (2.4 µg/gm) in the a.m. and native bovine CII (10 µg) in the p.m. After 1 week, all mice were immunized (intradermally at the base of tail) with 100 µg of bovine CII emulsified in complete Freund's adjuvant. Animals were placed in coded cages and were scored by a blinded observer twice weekly for the number of arthritic joints (joints swollen, red, and/or deformed).

Figure 7:
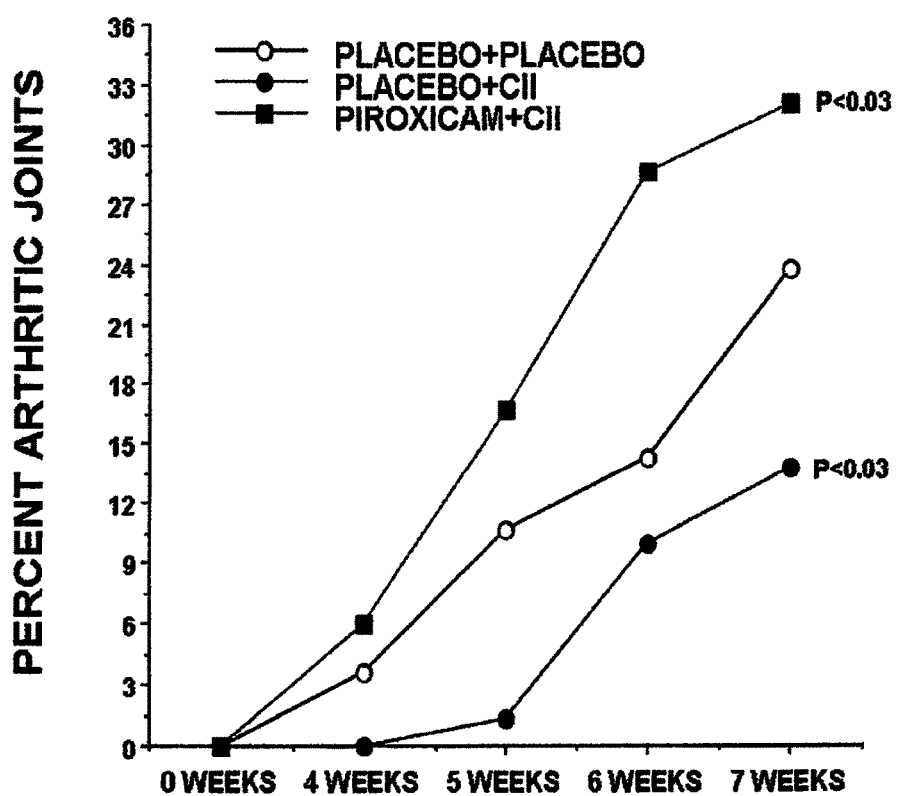
FIG. 7 is a chart showing abrogation of certain forms of oral tolerance by piroxicam.

As shown in FIG. 7, compared to Placebo+Placebo fed controls, the percent of arthritic joints was less over the observation period in the group of mice fed Placebo+CII ($p<0.03$ by Cochran-Mantel-Haenszel analysis). By contrast, there were significantly more arthritic joints over the same period of observation in mice fed Piroxicam+CII. In similar studies, we found that nabumatone (Relafen) also abrogated OT induction in DBA/1 mice (data not shown).

Example 4

IFNγ Production by Spleen Cells

To assess the effect of oral feeding of piroxicam to another group of mice fed Placebo or CII on spleen cell IFNγ production in a manner similar to the experiment in FIG. 7, four groups of mice (4 mice per group) were gavaged 8 days over 2 weeks with the following: Piroxicam a.m.—CII p.m.; Piroxicam a.m.—HAc p.m.; Saline a.m.—CII p.m.; or Saline a.m.—HAc p.m. After 1 week rest, all mice were immunized at the base of the tail with a CII—complete Freund's adjuvant emulsion. After 14 days, mice ere sacrificed, and spleen cells were isolated and set up in culture with PBS or α1(II)CB peptide mixture. After 72 h culture, harvested supernatants ere analyzed for IFNγ levels by ELISA.

Figure 8:
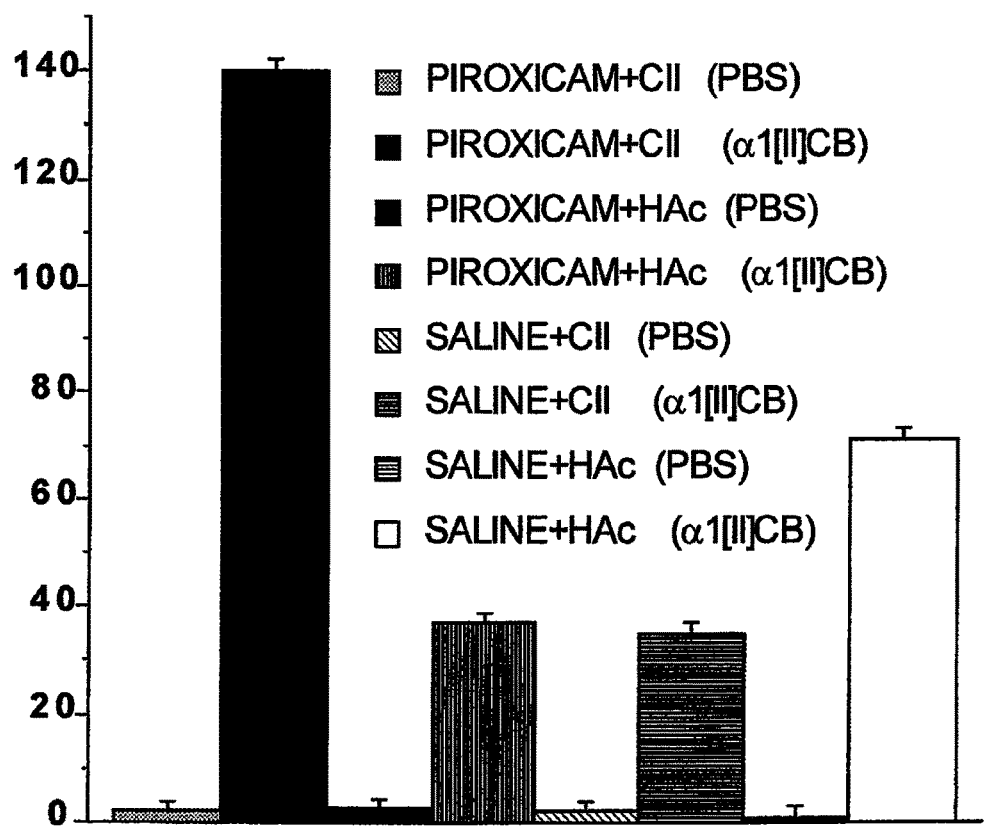
FIG. 8 is a chart showing IFN-γ production by al (II) stimulated spleen cells.

Mice fed CII+Placebo or piroxicam+Placebo had reduced production of IFNγ when their spleen cells were cultured in vitro with α1(II) CB peptide mixture. See, FIG. 8. When piroxicam was orally fed to mice being fed oral CII, however, there was a dramatic increase in the level of IFNγ production by spleen cells stimulated in vitro with α1(II)CB peptide mixture. In other experiments, it was found that the COX-2 inhibitor SC236 also blocked oral tolerance induction to CII in DBA/1 mice as assessed by IFNγ production by spleen cells (data not shown).

Example 5

COX-2 Inhibitor SC'236 Inhibits Oral Tolerance Induction

Groups of 8 mice each were gavaged on MTTHF×2 weeks in the a.m. with PBS or SC'236 (5 µg/gm in 100 µl PBS). SC'236 (Searle) is ~2000× more inhibitory for COX-2 than for COX-1.

Four of the mice given PBS in the a.m. and 4 mice given SC'236 in the a.m. were gavaged in the p.m. with 10 µg bovine type II collagen (CII). The other 4 mice in the a.m. PBS and a.m. SC'236 group were gavaged in the p.m. with 0.1M acetic acid (HAc) the vehicle the CII was dissolved in. After these 8 day feedings, all mice were rested for 1 week and then immunized with 100 µg of CII in complete Freund's adjuvant. After 10 days, all mice were sacrificed, and spleen cells ($2\times10^6$/ml) were isolated and set up in culture with PBS and bovine α1(II) (50 µg/ml) CB mixture. After 4 days culture, the supernatants were harvested and IFNγ levels determined by ELISA (Endogen). Since the PBS+ spleen cell culture from all mice produced between 1-12 pg/ml IFNγ, only the α1(II) data are plotted. All groups were compared to Placebo control group by Student's 2 sample t test.

Figure 9:
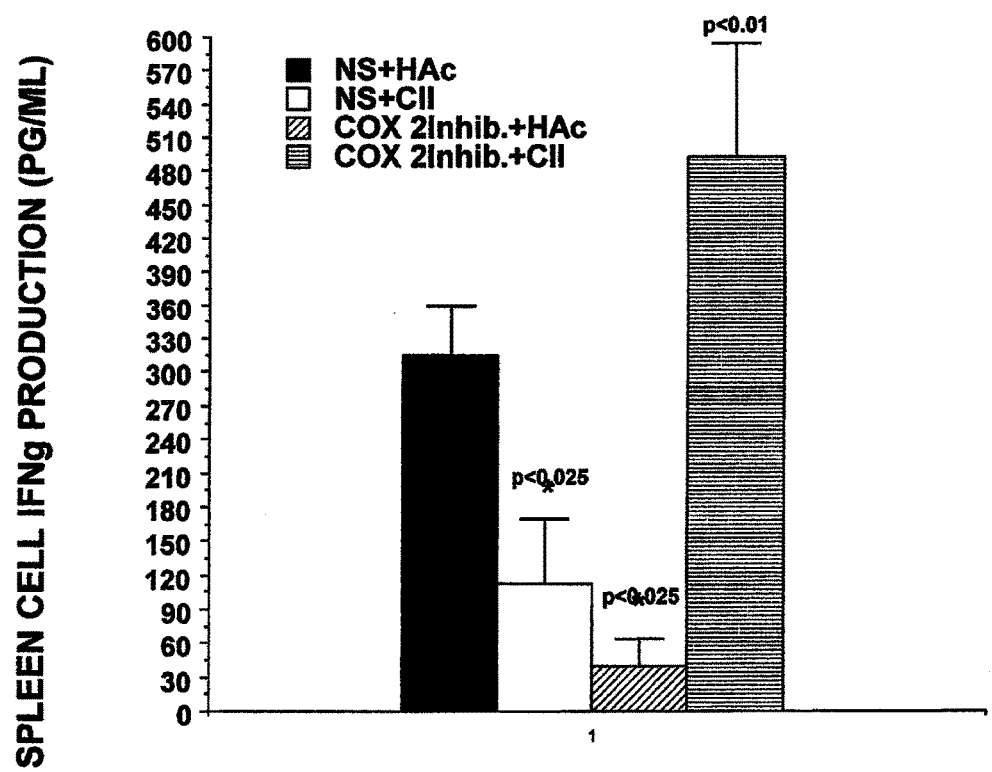
FIG. 9 is a chart showing COX-2 inhibitor SC'236 abrogates oral tolerance induction.

As shown in FIG. 9, feeding CII to DBA/1 mice induced oral tolerance manifested by a significant reduction in IFNγ production by spleen cells stimulated by α1(II) CB digest ($p<0.025$). In contrast, feeding SC'236 to the mice resulted in lower IFNγ production by α1(II) CB digest, but when mice were fed SC'236+CII there was a significant increase ($p<0.01$) in IFNγ production by spleen cells cultured with α1(II) CB digest. Given the caveat that SC'236 may also inhibit COX-1, but to a degree ~2000× less than it inhibits COX-2, these data suggest that COX-2 may be essential for optimal tolerance induction to low dose oral antigen.

Example 6

Persistent NSAID Effect on Oral Tolerance

Figure 10:
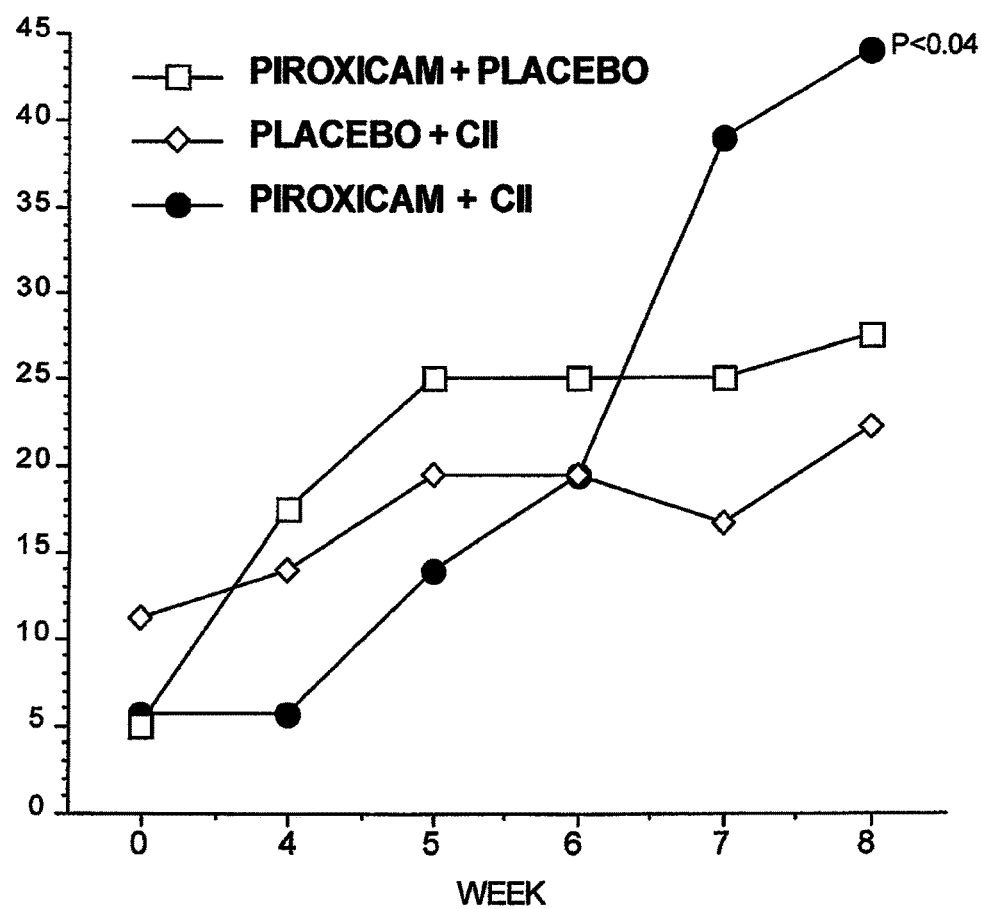
FIG. 10 is a chart showing persistent abrogation of oral tolerance by piroxicam.

To determine whether chronic feeding of piroxicam with CII would have a persistent effect on tolerance induction to CII in DBA/1 mice, three groups of 10-11 DBA/1 mice were fed 8 doses of CII over two weeks (as above) on two occasions separated by 6 months: piroxicam (2.4 µg/gm) a.m. and Placebo (0.1M HAc, 100 µl) p.m.; Placebo (saline) a.m. and native bovine CII (10 µg) p.m; or piroxicam (2.4 µg/gm) a.m. and native bovine CII (10 µg) p.m. Three months after the second 8 dose feeding, each mouse was immunized (intradermally at base of tail) with 100 µg native bovine CII emulsified in complete Freund's adjuvant. Mice were placed in coded cages and scored twice weekly by a blinded observer for numbers of arthritic joints. As shown in FIG. 10, at week 7 and 8, after immunization with CII, the group of mice that 9 and 3 months before were fed piroxicam plus CII had significantly more arthritic joints ($p<0.04$ at 8 weeks by chi square analysis) compared to the group of mice that were fed Placebo plus CII.

Example 7

GALT of Mice Fed with Piroxicam Plus CII

Figure 11:
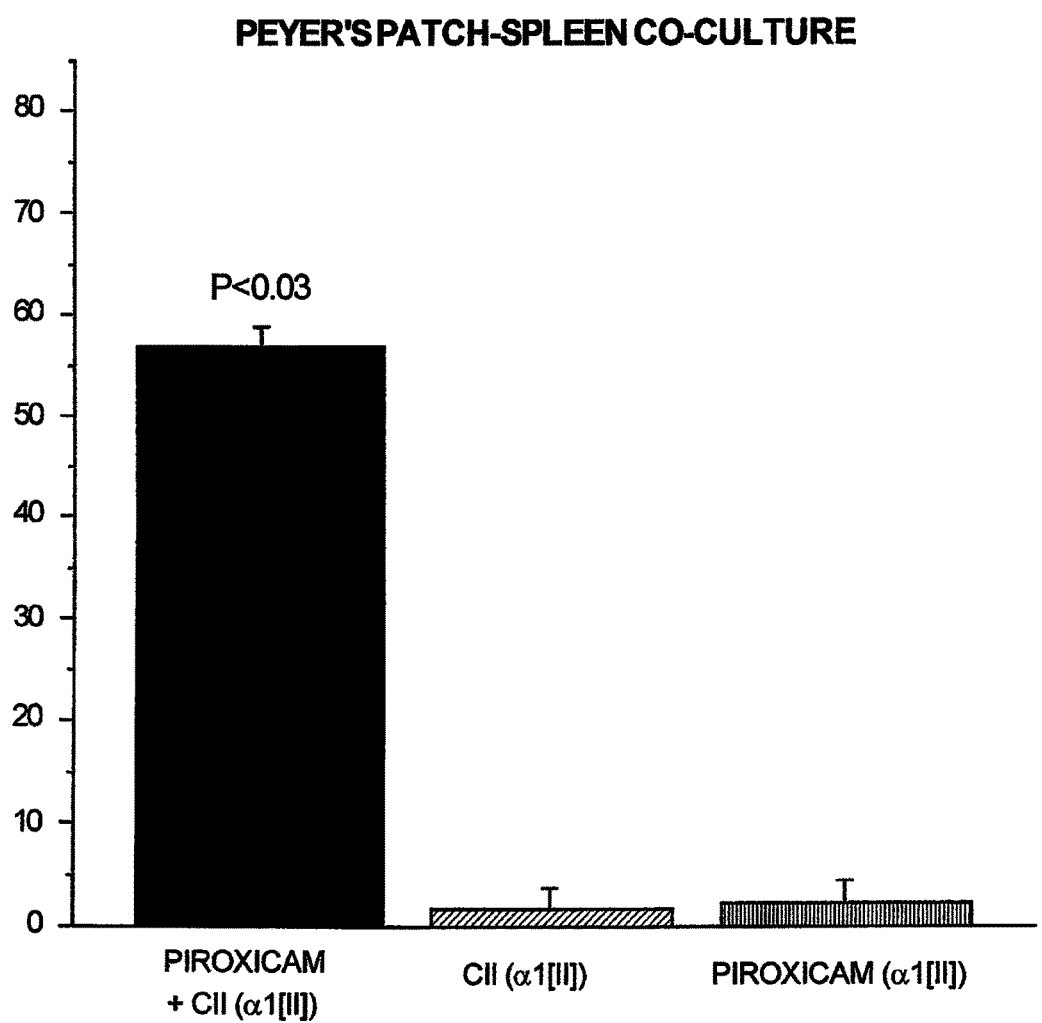
FIG. 11 is a chart showing the effect of piroxicam or CII on Peyer's patch spleen co-culture.
Figure 12:
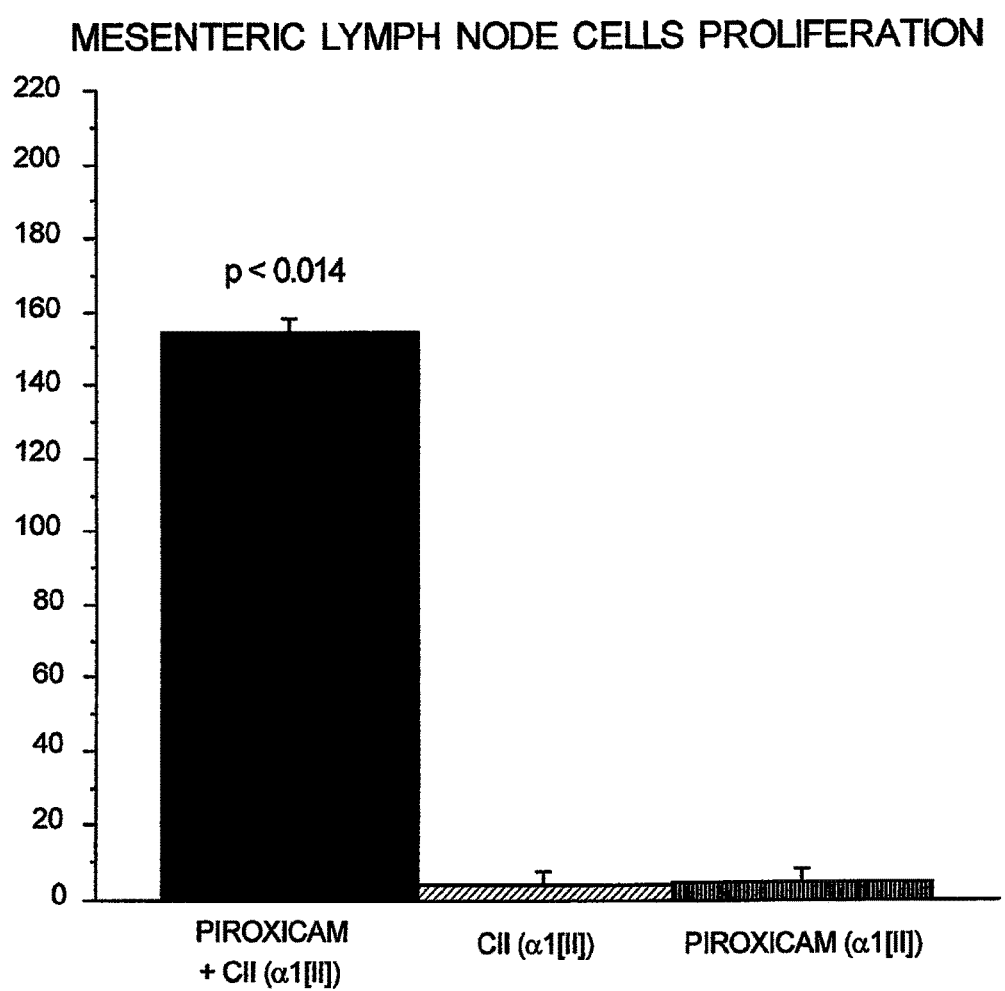
FIG. 12 is a chart showing the effect of piroxicam or CII on mesenteric lymph node cell proliferation

To assess the status of the GALT in these three groups of mice, Peyer's patch cells were isolated from each animal, and set up ($2.5\times10^5$/ml) in quadruplicate in co-culture with normal DBA/1 spleen cells ($2\times10^6$/ml) with addition of recombinant murine IL2 (10 U/ml). PBS (as a control) or 50 µg/ml bovine α1(II) CB peptide mixture were added to quadruplicate wells in 96 round bottom well plates. After 3 days, cultures were pulsed with $^3$H thymidine and harvested onto paper filters 24 h later. The "stimulation index" was calculated for each mouse by dividing the cpm of α1(II) CB peptide mixture culture by the cpm of the PBS control culture for each mouse. As shown in FIG. 11, compared to the co-culture of Peyer's patch cells from mice fed CII alone or piroxicam alone, there was marked stimulation by the α1(II) CB peptide mixture ($p<0.03$) of cells from mice fed piroxicam plus CII. Moreover, we have consistently found that Peyer's patch cells ($2.5\times10^5$/ml) from DBA/1 mice or Balb/c mice in co-culture with normal syngeneic spleen cells ($2\times10^6$/ml) when stimulated with murine IL-2 results in no stimulation of the spleen cells over background cpm. Thus, the marked increase in the stimulation index of Peyer's patch cells with DBA/1 spleen cells in the presence of α1(II) CB peptide mixture is quite exceptional and unexpected. The culture of mesenteric lymph node cells ($2\times10^6$/ml) from each mouse with the α1(II) CB peptide mixture revealed a similar pattern (FIG. 12). The mesenteric lymph node cells from mice fed either CII or piroxicam did not proliferate in response to the α1(II) CB peptide mixture. In contrast there was marked stimulation by α1(II) CB peptide mixture of mesenteric lymph node cells from mice fed piroxican plus CII (FIG. 12).

Further, studies were conducted using oral OVA (1 mg/day×5 days) in BALB/c mice and oral bovine CII (10 μg×8 doses over 14 days) in DBA/1 lac J mice to test the effects of commonly used immunomodulatory drugs on immune induction (prednisone 7.5 mg/day, hydroxychloroquine 400 mg/day, methotrexate 17.5 mg/week, leflunomide 20 mg/day after 100 mg/day×3 loading doses, sulfasalazine 2.5 gm/day, D-penicillamine 750 mg/day, IM gold, and etanercept 25 mg twice weekly). These immunomodulatory drugs did not completely suppress tolerance, and that it may be feasible to induce tolerance in RA patients to CII still taking these immunomodulatory drugs. Prednisone 10 mg/day equivalent in DBA/1 lac J mice and auranofin did block OT induction to CII.

Example 9

Administration of Oral Collagen II Reduces Autoimmunity in Patients with RA

Immunological tolerance, defined as a ≥30% reduction in IFN-γ production by PBMC cultured with α1(II) of type II collagen, was examined in patients. Patients that were taking disease-modifying antirheumatic drugs, anti-TNF agents and/or non steroidal inflammatories were administered misoprostol 100 μg bid to reverse the non steroidal antiinflammatory inhibition of oral tolerance. Patients were randomized to receive "low" or "high" doses of CII. The Low Dose group (n=38) took daily 30 μg/day bovine CII for 10 weeks, then 50 μg/day for 10 weeks and then 70 μg/day for 10 weeks. The High Dose group (n=41) took 90 μg/day for 10 weeks, 110 μg/day for 10 weeks and then 130 μg/day for 10 weeks.

Heparinized blood was obtained at baseline and after each of the 10 week treatment periods. The blood was diluted 1:3 with RPMI 1640 containing penicillin (100 u/ml) and streptomycin (100 μg/ml) within 1-4 hours after collection, wrapped in paper, and placed in a styrofoam box containing a "cold pack" and shipped overnight. The PBMC were isolated from the blood samples and set up in culture with bovine α1(II) 25 μg/ml, PHA 10 μg/ml or with 50 ul PBS. After 6 days in culture, cell free supernatants were collected and stored at −70° for up to 7 months at which time all samples from a given patient were assayed for IFNγ by commercial ELISA (R & D Systems). The results are shown as in FIG. 13.

The IFNγ stimulation index (SI) was calculated as $$\frac{\alpha1(II)IFN_\gamma - PBS\ IFN_\gamma}{PBS\ IFN_\gamma} \times 100.$$

The SI for patients receiving each of the low doses (30 μg, 50 μg and 70 μg/day) was compared with their SI at baseline before each of the 10 week treatments and similarly with the high dose CII group (90 μg, 110 μg and 130 μg/day) with their SI at baseline before each of the 10 week treatments.

There was marked suppression of IFNγ SI. After ten weeks treatment with 30 μg, 50 μg, 110 μg and 130 μg/day oral CII with ≥62 to 69% of patients exhibiting ≥50% reduction in α1(II) IFNγ SI. 70 μg and 90 μg/day doses did not reduce the IFNγ SI, and the 70 μg/day dose significantly increased the IFNγ SI compared to baseline values.

Further, the data showed that oral tolerance to CII, defined as a reduced immune response to fed antigen (CII), can be induced while patients are taking DMARDs, anti-TNF agents and NSAIDS if low dose misoprostol is given. The 30 and 50 μg/day doses had greater reduction in more categories.

The dose response showed maximal suppression of IFNγ production at 30 μg, 50 μg and 110 μg/day of oral CII. For the percent of patients that had a ≥50% reduction in IFNγ by α1(II)-stimulated PBMC, most patients could be tolerized (69% had a 50% reduction in α1(II) stimulated IFNγ production to orally administered CII) at these doses.

Figure 13:
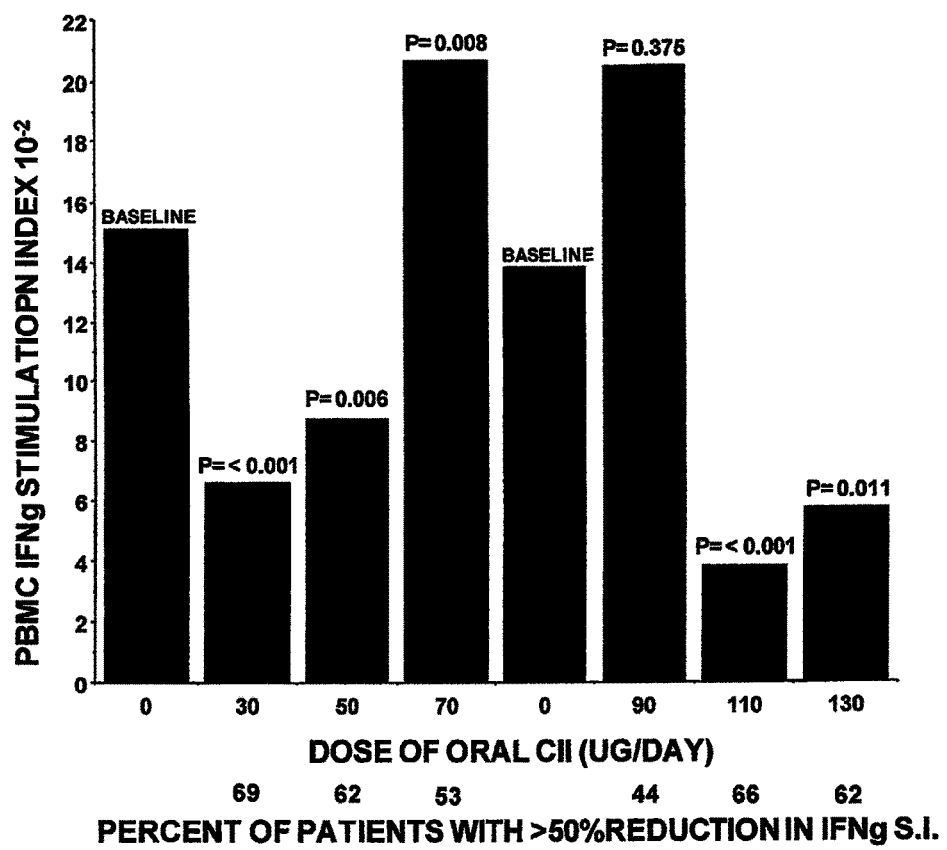
FIG. 13 is a chart showing the effect of oral collagen II treatment of rheumatoid arthritis patients and how it modulates PBMC IFN production by PBMC.

Further analysis of patients revealed that there were 30% non-responders to oral CII to the 30-50 μg/day dose of CII and 28% non-responders to the 110-130 μg/day dose (FIG. 13).

Example 10

Oral CII Tolerance is Associated with Response and No Response

To investigate if any particular genotype was associated with response or no response to oral CII in this cohort, 24 patients from Example 9 were selected.

Blood was obtained from the patients before administering bovine CII orally to RA patients who produced ≥2× increase in IFNγ by α1(II) stimulated compared to PBS control PBMC cultures. Isolated (10 μg/mL), bovine α1(II) (50 μg/mL), bovine α1(II) CB11 (50 μg/mL) or with 25 μl PBS added to culture at 2×10⁶ per 500 μl 48 well tissue culture plates of Dulbecos MEM supplemented with penicillin (100 μg/mL), streptomycin (100 μg/mL) and 9% fetal calf serum. After 6 days, supernatants were harvested, centrifuged at 2000×G for 5 minutes and levels of IFNγ were quantitated by commercial ELISA (R & D Systems). Differences in IFNγ levels and in SI for PHA, α1(II) and α1(II) CB11 between responders and non-responders were analyzed for significance using Mann-Whitney rank sum test.

Of the 24 patients, 16 patients responded to oral CII with reduction of α1(II) and α1(II) CB11 stimulated IFNγ production by PBMC cultures and 8 patients did not reduce IFNγ by PBMC culture with these antigens. The baseline IFNγ levels of the 16 responders and 8 non-responders to PBS, α1(II) 50 μg/ml α1(II) CB11 50 μg/ml and PHA 10 μg/ml in six day PBMC cultures are given in Table I.

The IFNγ stimulation index (S.I.) calculated for PHA as follows:

$$\frac{PHA\ IFN_\gamma - PBS\ IFN_\gamma}{PBS\ IFN_\gamma} \times 100;$$

for α1(II) as follows:

$$\frac{\alpha1(II)IFN_\gamma - PBS\ IFN_\gamma}{PBS\ IFN_\gamma} \times 100;$$

and for α1(II) CB11 as follows:

$$\frac{\alpha1(II)CB11 IFN_\gamma - PBS\ IFN_\gamma}{PBS\ IFN_\gamma} \times 100.$$

As shown in Table II, the CII oral tolerance non-responders had lower mean baseline IFNγ α1(II) S.I.s than the CII oral tolerance responders (190±40 vs 1800±520, p=0.002). CII oral tolerance non-responders had lower mean baseline IFNγ α1(II) CB 11 S.I.s than the CII oral tolerance responders (1060±197 vs 210±90, p=0.003). The IFNγ PHA S.I.s at baseline were not different between the CII oral tolerance responders and non-responders.

TABLE II

Comparison of IFNγ Production at Baseline Between CII OT Responders and Non-Responders

| Culture Adds | CII OT Responders (N = 16) | | CII OT Non-Responders (N = 8) | |
|---|---|---|---|---|
| | IFNγ PG/mL | IFNγ S.I. | IFNγ PG/mL | IFNγ S.I. |
| PBS | 142 ± 41 | — | 203 ± 159 (p = 0.395) | — |
| α1(II) | 1774 ± 501 | 1800 ± 520 | 581 ± 183 (p = 0.150) | 190 ± 40 (p = 0.002) |
| α1(II) CB11 | 1391 ± 295 | 1060 ± 197 | 523 ± 167 (p = 0.06) | 210 ± 90 (p = 0.003) |
| PHA | 6979 ± 2291 | 6400 ± 3100 | 3150 ± 1278 (p = 0.520) | 4200 ± 3200 (p = 0.349) |

Example 11

The Microarray Assessment Produced Accurate Data for Analysis of Genotypes of RA Patients SNP analysis was performed of 16 responders and 8 non-responders to oral CII to find the frequency of SNPs closely associated on chromosomes next to several cytokines and chemokines known to be important for oral tolerance induction. The 16 patients were those with had ≥50% reduction in IFNγ α1 stimulation index from baseline to either the 30 μg/day, 50 μg/day, 110 μg/day or 130 μg/day dose of CII ("OT Responders"). The 8 patients with increases in IFNγ α1 S.I. at the 30 μg/day, 50 μg/day, 110 μg/day or 130 μg/day doses of oral CII were selected ("OT Non-Responders").

Commercial whole genome mapping chips were used to map the potential genetic loci in a timely and economic manner. The genome of the two groups of Example 2 were analyzed by DNA extraction using a commercial DNA extraction kit, the Qiagen kit (Qiagen Inc., Alameda, Calif.) following the manufacturer's instructions. After determining the quality and quantity of the DNA in an Eppendorf photometer (Eppendorf Scientific Inc., Westbury, N.Y.), and by electrophoresis, DNA with OD260/280 ratios ratio >1 and high integrity was used for genotyping. For each sample, 250 ng of DNA was used for genotyping using Affy GeneChip® Mapping 10K 2.0 Array, a SNP-based genetic mapping tool. The 10K 2.0 Array contains genotypes greater than 10,000 human single nucleotide polymorphisms (SNPs) on a single array. The tool may be used to identify regions of the genome that are linked to or associated with, a particular trait or phenotype, in our case, the CII oral tolerance resistance.

The protocol included four major procedures: in silico fractionation, synthesis of predicted fragments on microarrays, biochemical fractionation, and Allele specific hybridization and Genotype Calling. Two different signals that represent each of two polymorphisms of 10,000 single nucleotides were produced. The software creates the polymorphism or genotype of every of 10,000 single nucleotides. The genotype of polymorphism of each of 10,000 SNPs of every sample was called into three types, homozygous type I, AA; homozygous type II, BB; and heterozygous, AB, as indicated in table III.

TABLE III

Genotyping of 15 Patients

| Patient # | Called Gender | SNP Call | Signal Detection | AA Call | AB Call | BB Call |
|---|---|---|---|---|---|---|
| 001-101 | M | 94.41% | 99.67% | 33.27% | 32.90% | 33.83% |
| 023-117re | M | 93.70% | 99.59% | 33.54% | 32.89% | 33.56% |
| 046-123 | F | 78.89% | 99.25% | 32.53% | 35.37% | 32.10% |
| 073-127 | M | 93.57% | 99.40% | 34.21% | 31.30% | 34.49% |
| 090-323 | F | 95.87% | 99.89% | 32.21% | 33.99% | 33.80% |
| 095--325 | F | 94.57% | 99.05% | 32.66% | 33.82% | 33.51% |
| 109-319 | F | 85.35% | 97.53% | 34.89% | 30.66% | 34.45% |
| 121-329 | M | 93.44% | 99.55% | 33.70% | 32.28% | 34.02% |
| 127-137 | M | 93.82% | 99.57% | 33.35% | 33.30% | 33.34% |
| 142-343 | M | 94.93% | 99.80% | 34.12% | 31.86% | 34.02% |
| 143-339 | M | 96.28% | 99.92% | 32.76% | 34.00% | 33.25% |
| 146-139 | M | 92.07% | 99.05% | 33.45% | 32.09% | 34.45% |
| 148-341 | F | 91.31% | 99.18% | 33.38% | 33.21% | 33.41% |
| 154-347 | F | 96.89% | 99.95% | 33.06% | 34.18% | 32.76% |

Table III is the genotyping of 15 patients (9 males, 6 females). The detectable single of SNPs in most samples was over than 99%, indicating a high quality of detection. The SNP call indicates that the percentage among 10,000 of SNPs that could be recognized and for which data were given. More than 90% of SNPs in those samples was detected by the experiment. The distribution of three genotypes, the AA, AB, and BB was about one third (33%) for each of them.

Example 12

Association Between SNP A-1515737 and Oral CII Responders and Non-Responders

To find the possible polymorphism that linked non-tolerogenic response to CII treatment, the genotype of the patients of Example 3 was sorted into oral CII responders and non-responder groups. For each group, the total number of three genotypes, AA, AB, and BB was calculated for each SNP on the chip. Table IV shows the genotype ratio of SNP in each of those candidate genes.

TABLE IV

Polymorphism of Candidate Genes.

| Candidate Gene name | SNP IDs | AA-AB-BB (responder/non-responders) |
|---|---|---|
| TGF beta 1, 2 3 | SNP_A-1511117 | 3--4—6/3--2--4 |
| | SNP_A-1515879 | 8--6—0/9--1--0 |
| ICOS | SNP_A-1509114 | 3--4—5/0--8--2 |
| | SNP_A-1509255 | 6--7—1/2--6--2 |
| | SNP_A-1513931 | 13—1—0/9--1--0 |
| | SNP_A-1515899 | 0--0—14/0--0--10 |
| | SNP_A-1519289 | 2--1—7/2--4--4 |

TABLE IV-continued

Polymorphism of Candidate Genes.

| Candidate Gene name | SNP IDs | AA-AB-BB (responder/non-responders) |
|---|---|---|
| IL-4R | SNP_A-1509275 | 3--9—1/7--3--0 |
| IL-10R | SNP_A-1518241 | 2--3—7/4--3--2 |
| CCL2 | SNP_A-1514598 | 1--5—8/3--4--3 |
| IFN gamma | SNP_A-1508498 | 8--5—1/8--2--0 |
|  | SNP_A-1512645 | 3—11—2/0--4--4 |
|  | SNP_A-1512719 | 2—10—2/5--5--0 |
|  | SNP_A-1515330 | 3--9—2/5--4--0 |
|  | SNP_A-1515737 | 1--9—6/6--1--1 |
|  | SNP_A-1518829 | 2—10—4/0--2--6 |
|  | SNP_A-1518878 | 3—10—1/7--2--1 |
| Glutamic Acid decarboxylse | SNP_A-1513856 | 14—0—0/10--0—0 |
|  | SNP_A-1509772 | 2--8—4/1--6—3 |
| IL-1ra | SNP_A-1511280 | 2--5—7/0--3--7 |

As shown in Table IV, in 20 SNPs of 8 candidate genes, the most genotypic patterns between responder and non-responders are the same or similar. The patterns of the first SNP of Glutamic Acid decarboxylse is 14-0-0 (for AA-AB-BB) and 10-0-0; the second SNP is 2-8-4 and 1-6-3. However, there is a large difference of genotype distribution of the SNP_A-1515737 between response and non-response groups, being 1-9-6 and 6-1-1 respectively for responders and non-responders. While most of response patients have genotype either heterozygous (thus, the AG) or homozygous of BB (Thus the GG genotype), the majority of patients in non-response group had a AA genotype. Further analysis focused on the SNP_A-1515737.

The sequences of SNP_A-1515737 is as the following: TTTTTTTTTGTACCTRGTTCTATGGTTACCTT (SEQ ID NO: 21). The R represents the polymorphic site that can be either A (resulting in SEQ ID NO. 1) or G (resulting in SEQ ID NO. 2). Thus, AA represents AA homozygous, while AB represents A/G heterozygous and BB represents GG genotype, A→G represents the polymorphism site.

Example 13

Figure 14:
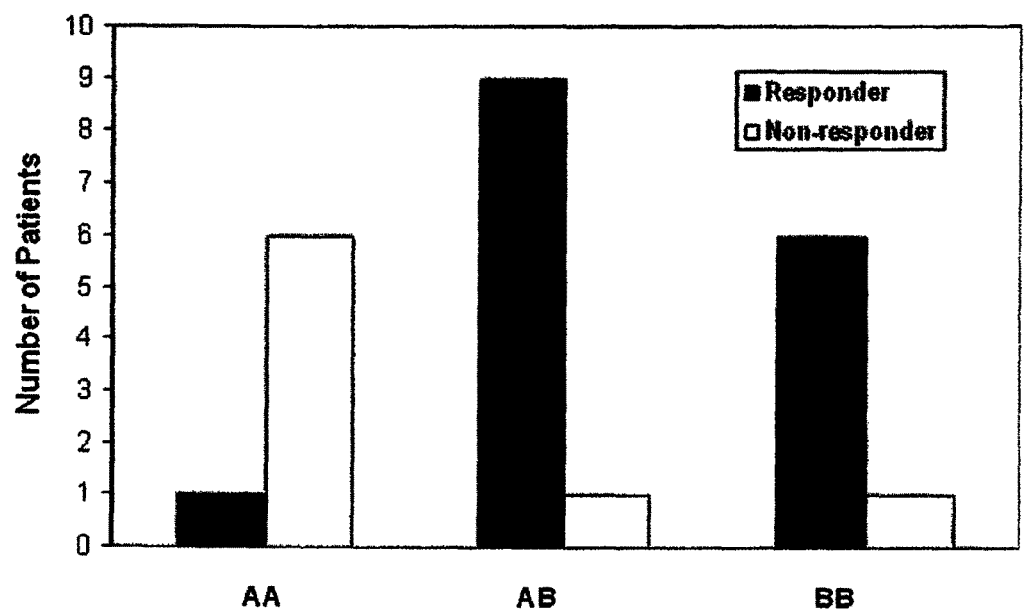
FIG. 14 is a chart the genotyping of persons with rheumatoid arthritis and their ability to induce immune tolerance.

Distribution of SNP_A-1515737 Among CII Oral Tolerance Responder and Non-Responder Patient Genotype patterns of responders and non-responders were compared and a significant difference in the genotype distribution found. See, FIG. 14. To calculate the P values, a number was assigned to the three genotypes. The AA genotype was assigned 1, AB (thus, AG) was assigned 2, and the BB (Thus GG genotype) was assigned 3. According to those assumptions, the P values of SNP A-1515737 reached 0.052.

The 24 patients were grouped into those had the AA genotype (or A→G) of SNP A-1515737 and those that did not have the AA genotype (i.e. were AB or BB). Table V and VI summarize the data based on the two groups. Table V lists the baseline IFNγ levels in six day supernatants PBMC stimulated for six days with PHA, α1(II), α1(II) CB11 or no additions (PBS). Patients with SNP A-1515737 AA had significantly lower IFNγ α1(II) S.I. values (mean 270±90), compared to those patients not having three SNP A-1515737 AA (mean 1674±505, p=0.028 by Mann-Whitney Rank Sum Test). Of the 7 patients with SNP A-1515737 AA only one had CII oral tolerance response and of the 17 patients who have SNP A-1515737 GG only 2 more non CII or α1 tolerance responders.

TABLE V

Baseline IFNγ (PG/ML) in 6 Day PBMC Culture Supernatants

| Patient # | Genotype | PHA | PHA SI | A1(II) | α1 (II) SI | α1(II) CB11 | α1(II) CB11 SI | PBS | OT Responder |
|---|---|---|---|---|---|---|---|---|---|
| \multicolumn{10}{c}{No of SNP A-1515737 AA Genotype} |
| 073-127 | BB | 16278 | 2533 | 3937 | 6052 | 4574 | 7047 | 234 | Yes |
| 001-101 | AB | 486 | 817 | 1348 | 2443 | 292 | 451 | 53 | Yes |
| 023-117 | AB | 14638 | 47119 | 256 | 726 | 389 | 1155 | 31 | Yes |
| 039-303 | AB | 446 | 1012 | 98.5 | 146 | 51 | 27 | 40.1 | No |
| 046-123 | BB | 7679 | 1474 | 1474 | 203 | 486 | −0.4 | 488 | No |
| 090-323 | BB | 1163 | 2054 | 1483 | 2646 | 1451 | 2587 | 54 | Yes |
| 109-319 | BB | 4444 | 11443 | 61 | 58 | 123 | 219 | 38.5 | Yes |
| 121-329 | AB | 6983 | 3017 | 1728 | 671 | 2243 | 901 | 224 | Yes |
| 127-137 | BB | 618 | 301 | 505 | 228 | 500 | 225 | 154 | Yes |
| 143-339 | AB | 1056 | 1752 | 4188 | 7247 | 1273 | 2133 | 57 | Yes |
| 142-343 | AB | 189 | 133 | 325 | 301 | 383 | 373 | 81 | Yes |
| 148-341 | BB | 23427 | 8876 | 1019 | 290 | 1523 | 484 | 261 | Yes |
| 146-139 | AB | 1431 | 3821 | 630 | 1626 | 1271 | 3382 | 36.5 | Yes |
| 154-347 | AB | 3774 | 6521 | 284 | 398 | 843 | 1379 | 57 | Yes |
| 072-128 | BB | 2755 | 300 | 7688 | 1017 | 2205 | 220 | 688 | Yes |
| 113-332 | AB | 245 | 113 | 2641 | 2197 | 1865 | 1522 | 115 | Yes |
| 040-302 | AB | 29527 | 64089 | 1058 | 2200 | 433 | 841 | 46 | Yes |
|  |  | 6723 ± 2165 | 9140 ± 4373 | 1690 ± 481 | 1674 ± 505 | 1171 ± 274 | 1350 ± 425 | 146 ± 94 |  |
| \multicolumn{10}{c}{SNP A-1515737 AA Genotype} |
| 097-320 | AA | 273 | 82 | 1208 | 265 | 1268 | 280 | 331 | No |
| 050-308 | AA | 707 | 1314 | 90 | 80 | 120 | 140 | 50 | No |
| 058-309 | AA | 2093 | 776 | 455 | 90 | 294 | 23 | 239 | No |
| 061-311 | AA | 3173 | 1256 | 671 | 187 | 1240 | 430 | 234 | No |
| 095-325 | AA | 1744 | 1103 | 1228 | 747 | 2894 | 1896 | 145 | Yes |
| 155-348 | AA | 1050 | 405 | 461 | 122 | 428 | 106 | 208 | No |
| 014-109 | AA | 9777 | 26686 | 182 | 399 | 293 | 703 | 36.5 | No |
|  |  | 2688 ± 1236 | 4517 ± 3699 | 614 ± 172 | 270 ± 90 | 934 ± 371 | 511 ± 247 | 245 ± 40 |  |
|  |  | p = 0.546 | p = 0.240 | p = 0.172 | p = 0.028 | p = 0.391 | p = 0.153 | p = 0.070 |  |

In Table VI, the same patients were arranged and their IFNγ α1(II) S.I. at baseline and after oral CII administration (30 μg, 50 μg or 110 μg/day for 10 weeks) was compared. As shown in Table VI, patients who did not have SNP A-1515737 AA (ROT1 AA) genotype had a significant reduction in the IFNγ α1(II) S.I. after oral CII compared to baseline values (p<0.001 by Wilxocon Rank Sum Test). In contrast, patients who carried the SNP A-1515737 AA had no significant change in IFNγ α1(II) S.I. after oral CII treatment (p=0.230 by Wilcoxon Rank Sum Test). This was also reflected when data are represented as a ratio of IFNγ α1(II) S.I. after oral CII/baseline (p=0.011).

TABLE VI

REDUCTION IN α1(II) SI AFTER ORAL CII IN PATIENTS WITH RA

| Patient # | Genotype | α1(II) SI Baseline | After Oral CII | OT Responder | Ratio: After/baseline |
|---|---|---|---|---|---|
| \multicolumn{6}{c}{No SNP A-1515737 AA Genotype} | | | | | |
| 073-127 | BB | 6065 | 18 | Yes | 0.0030 |
| 001-101 | AB | 2443 | 246 | Yes | 0.1008 |
| 023-117 | AB | 726 | 360 | Yes | 0.4932 |
| 039-303 | AB | 146 | 280 | No | 1.9178 |
| 046-123 | BB | 203 | 590 | No | 2.9064 |
| 090-323 | BB | 2646 | 152 | Yes | 0.0573 |
| 109-319 | BB | 58 | 6 | Yes | 0.1034 |
| 121-329 | AB | 671 | 276 | Yes | 0.4119 |
| 127-137 | BB | 228 | 18 | Yes | 0.0789 |
| 143-339 | AB | 7247 | 503 | Yes | 0.0694 |
| 142-343 | AB | 301 | 19 | Yes | 0.0631 |
| 148-341 | BB | 290 | 0 | Yes | 0 |
| 146-139 | AB | 1626 | 3 | Yes | 0.0018 |
| 154-347 | AB | 398 | 7 | Yes | 0.0176 |
| 072-128 | BB | 1017 | 358 | Yes | 0.3520 |
| 113-332 | AB | 2197 | 93 | Yes | 0.0423 |
| 040-302 | AB | 2200 | 540 | Yes | 0.2454 |
| | | 2081 ± 505 | 175 ± 46 | | 0.427 ± 0.217 |
| | | | | | p = 0.011 |
| | | p ≤ 0.001 | | | |
| \multicolumn{6}{c}{SNP A-1515737 AA Genotype} | | | | | |
| 097-320 | AA | 265 | 630 | No | 2.3774 |
| 050-308 | AA | 80 | 404 | No | 5.0500 |
| 058-309 | AA | 90 | 268 | No | 2.9778 |
| 061-311 | AA | 187 | 2020 | No | 10.8021 |
| 095-325 | AA | 747 | 3 | Yes | 0.0040 |
| 155-348 | AA | 122 | 167 | No | 1.3688 |
| 014-109 | AA | 399 | 800 | No | 2.0050 |
| | | 270 ± 90 | 613 ± 256 | | 3.512 ± 1.347 |
| | | p = 0.230 | | | |

The data was analyzed by use of Chi Square with Fisher's exact test, there is a highly significant difference (p=0.0017) between oral CII responders and non-responders in patients with SNP A-1515737 AA genotype and those not having this genotype (Table VII).

TABLE VII

Chi Square of SNP A-1515737 AA Genotype vs Non SNP A-1515737 AA Genotype

| | AA | Non-AA |
|---|---|---|
| CII OT Non-Responder | 7 | 2 |
| CII OT Responder | 1 | 15 |

Example 14

Differences Between Responders and Non-Responders SNPs

The genotype patterns of other SNPs within close distance to A-1515737 was also examined. In addition to A-1515737, there are six other SNP within the same genome region. None of them has a significant association with the response or non-response to CII treatment. For example, SNP A-1508498, which is 146068 by at 5' side of DYRK2 and 350588 bp at 3' side: IFNγ, is located very close to A-1515737, which is 265143 bp at 5' side of DYRK2 and 231513 bp at 3' side of IFNγ. The genotype patterns of responders and non-responders are similar, with AA, AB, and BB of 8-5-1 and 8-2-0, respectively.

The segregating patterns of an average of 10 SNP along each chromosome was examined, but there was no evidence of an association of any segregating pattern with the CII response.

Eight SNPs relevant to the non-response histocompatibility complex (HLA class II histocompatibility) was examined but there was no evidence of an association of the segregating bands with the CII response.

Example 15

SNP A-1515737 and Linkage to Oral Tolerance Resistance in Other Autoimmune Diseases Samples from 26 patients from a trial of oral type I collagen (CI) in patients with diffuse systemic sclerosis (SSc) who took 500 μg/day CI for 12 months were collected. Six of the 26 had A-1515737 AA genotype (Table VII). No patients were on DMARDs, biologies, NSAIDS or prednisone.

PBMCs were collected from the patients and cultured with native bovine CI and α2(I) CB mixture and a trend toward defective production IL-10 PBMC cultured with α1(I) CB mixture.

Patients who were tolerized by oral CI had upregulation of the Th2 cytokine, IL-10 by PBMC stimulated with CI, or α1(I) or α2(I). As shown in table VII, SSc patients with ROT1AA genotype and did not upregulate IL-10 production by α2(I) or CI stimulated PBMC in SSc patients after 12 months of treatment with oral CI. THE SNP A-1515737 was also examined in 53 additional SSc patients and found the overall prevalence of AA was 32%, 35%

TABLE VII

IL-10 PRODUCTION CHANGE AFTER 12 MONTHS OF ORAL CI and 12 MONTHS FOR SSc PATIENTS WITH and WITHOUT ROT1 AA*

| | Bovine Native CI IL-10 pg/ml |
|---|---|
| Genotype AA Patient # | |
| N = 6 | −825 ± 338 |
| Genotype BB or BA Patient # | |
| Mann Whitney | 27 ± 97 |
| Rank Sum Test | p = 0.008 |
| Fisher's Exact Test | p = 0.014 | were GG and 30% were GA. Like in RA patients, SSc patients with AA exhibited less upregulation of IFNγ production by α2(I)-stimulated PBMC (Tables VII and VIII).

TABLE VIII

IFNγ Production by Hα1(I)-Stimulated PBMC from SSc Patients at Baseline

|  | # of Patients | IFNγ pg/ml |
|---|---|---|
| ROT1AA+ | 25 | 16 ± 134 |
| ROT1GG or GA | 54 | 3146 ± 2574 |
| Mann Whitney Rank Sum Test |  | p = 0.036 |

* PBMC of patients enrolled in Phase II CI/SSc Study were cultured with 25 μg/ml human α1(I) for 6 days after which culture supernatants were harvested and IFNγ levels determined by ELISA.

Example 16

IL-10 Production After 12 Months of Oral CI and 12 Months for SScPatients with and without ROT1 AA Patients with ROT1 AA, GG or GA genotype had IL-10 measured of IL-PBMC cultures stimulated by α1(I) CB mixture, α2(I) CB mixture, or native CI after receiving oral CI for 12 months minus the values of IL-10 in the supernatants of PBMC cultures stimulated with the same antigens at baseline before oral CI was administered to the SSc patients.

Patients with ROT1 AA genotype received oral bovine CI 500 ug/day for 12 months had deficient upregulation of IL-10 production by their PBMC when cultured with native bovine CI and α2(I) CB mixture and a trend toward defective production IL-10 PBMC cultured with α1(I) CB mixture, demonstrating that ROT1 AA is associated with impaired oral tolerance to protein antigen. See, Table IX.

TABLE IX

IL-10 PRODUCTION CHANGE AFTER 12 MONTHS OF ORAL CI and 12 MONTHS FOR SCLEROSIS PATIENTS WITH and WITHOUT ROT1AA*

|  | Bovine α1(I) CB Mix IL-10 pg/ml | Bovine α2(I) CB Mix IL-10 pg/ml | Bovine Native CI IL-10 pg/ml |
|---|---|---|---|
| Genotype AA Patient # |  |  |  |
| 071109 | −342 | −1692 | −1726 |
| 130403 | −19 | +28 | +70 |
| 061009 | −611 | −494 | −920 |
| 060507 | −112 | +490 | −233 |
| 060403 | −2942 | −3736 | −1886 |
| 040104 | +295 | −448 | −253 |
|  | −622 ± 480 | −975 ± 627 | −825 ± 338 |
| Genotype GG or GA Patient # |  |  |  |
| 020705 | −314 | −388 | −135 |
| 030504 | +410 | +203 | +566 |
| 070101 | −104 | −86 | −334 |
| 080101 | −391 | −180 | +192 |
| 011008 | +529 | +859 | +103 |
| 021308 | +216 | +546 | +386 |
| 040806 | −968 | −1000 | −1564 |
| 020906 | +347 | +261 | +233 |
| 021411 | −397 | −2021 | +21 |
| 041308 | +1364 | +1460 | +237 |
| 072317 | +108 | +145 | +150 |

TABLE IX-continued

IL-10 PRODUCTION CHANGE AFTER 12 MONTHS OF ORAL CI and 12 MONTHS FOR SCLEROSIS PATIENTS WITH and WITHOUT ROT1AA*

|  | Bovine α1(I) CB Mix IL-10 pg/ml | Bovine α2(I) CB Mix IL-10 pg/ml | Bovine Native CI IL-10 pg/ml |
|---|---|---|---|
| 061211 | −205 | −113 | −94 |
| 072014 | −81 | +141 | +32 |
| 090605 | −561 | −509 | −282 |
| 091310 | +582 | +5 | +232 |
| 030103 | −46 | +381 | +192 |
| 030201 | −538 | +252 | −52 |
| 050303 | −227 | −115 | +43 |
| 072418 | +663 | −415 | +269 |
| 080403 | +221 | +141 | +341 |
| Mann Whitney Rank Sum Test | 30 ± 119 p = 0.062 | 22 ± 156 p = 0.039 | 27 ± 97 p = 0.008 |
| Fisher's Exact Test | NS | NS | p = 0.014 |

Example 17

ROT1 Genotype in Patients and Family Members with Chron's Disease

We assessed SNP A-1515737 (ROT1) genotype in patients and/or family members with Crohn's and/or ulcerative colitis and healthy controls with no IBD or other known autoimmune disease. Table X summarizes the genotype results in Crohn's diseases using DNA from buccal swabs, showing the ROT1 AA distribution was 91.67% for patients with Chron's Disease.

TABLE X

| ROT1 Genotype | Total (%) |
|---|---|
| Distribution of ROT1 Genotypes in Patients with Definite Crohn's Disease | |
| AA | 8 |
| AG | 0 |
| GG | 0 |
| Distribution of ROT1 Genotypes in First Degree Relatives of Patients with Crohn's Disease or Crohn's plus Ulcerative Colitis | |
| AA* | 9 |
| AG | 0 |
| GG | 0 |

* Relatives have CD or CD and UC

Of all the Crohn's disease patients and their first degree relatives genotyped, 91.67% have ROT1AA. This evinces that ROT1AA is associated with oral tolerance resistance in Crohn's disease.

The prevalence of ROT1AA in 12 Crohn's disease and first degree relatives (91.6%) was greater than 79 patients with SSc (31.6%), 54 patients with RA (38.9%) and in healthy controls (35.7%) (See Table XI).

TABLE XI

Distribution of ROT1 Genotype in Patients with Systemic Sclerosis, Rheumatoid Arthritis and Healthy Controls

| ROT1 Genotype | Systemic Sclerosis | | Rheumatoid Arthritis | | Normal Controls | |
|---|---|---|---|---|---|---|
| | Total | Percent | Total | Percent | Total | Percent |
| AA | 25 | 31.6% | 21 | 38.9% | 5 | 35.7% |
| AG | 24 | 30.3% | 17 | 31.5% | 6 | 42.86% |
| GG | 30 | 38% | 16 | 29.6% | 3 | 21.43% |

Example 18

ROT1 Genotype is Present in 31% of Patients with Diffuse SSc

Banked PBMC cell pellets were surveyed for all the patients with diffuse SSc, and 32% were found to be homozygous for ROT1 AA, 35% were homozygous for ROT1 GG, and 30% were heterozygous ROT1 GA.

Figure 16:
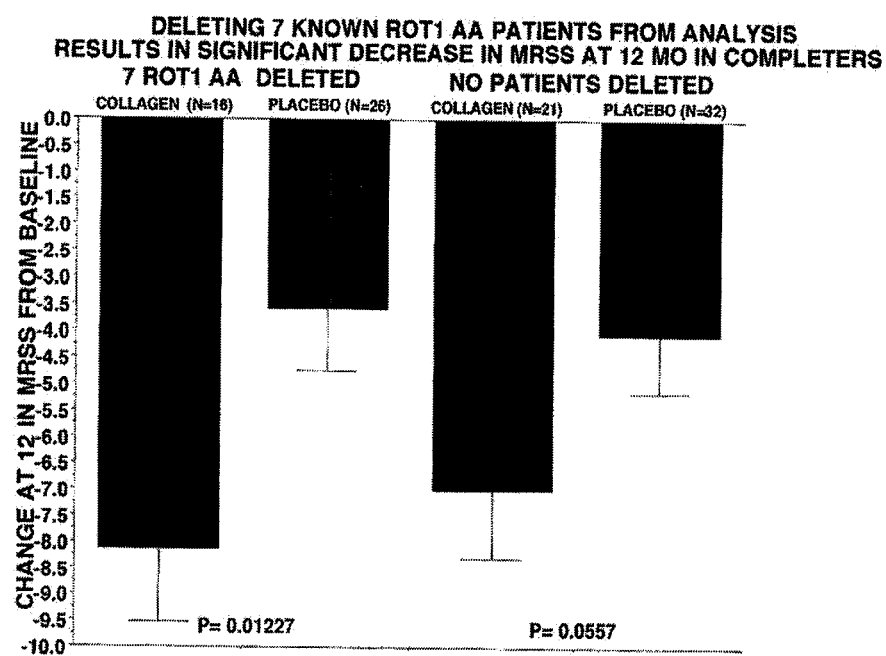
FIG. 16 is a chart showing a significant reduction in MRSS at 12 months versus placebo patients.

The SSc patients with ROT1 AA exhibited less upregulation of IFNγ production by α1(I)-stimulated PBMC. In the Phase II oral CI tolerance clinical trial at 12 months, 79 SSc patients were genotyped of the 168 enrolled in the clinical trial. Seven of the 23 ROT1AA genotype were in the Late Phase category, and deleted from the results. Reanalysis of the completers shows a significant difference in the change in MRSS at 12 months from baseline values in the CI treated patients when compared to the placebo treated patients using the Wilcoxon Rank Sum test (see FIG. 16).

TABLE 1

| Antigen | Disease |
|---|---|
| 1D protein | Endocrine orbitopathy |
| 59-kD renal antigen | Progressive glomerulonephritis |
| Acetylcholine receptor subunit | Myasthenia gravis |
| Aggrecan, fibrillin and metalloproteinase-3 | Juvenile idiopathic arthritis |
| Alpha3 (IV) NI1 | Anti-GBM disease |
| Alpha-enolase | Asthma |
| Alpha-fetoprotein | Juvenile Batten disease |
| Annexin A6 | Neonatal lupus erythematosus |
| Apoptotic cell-binding protein | Systemic lupus erythematosus |
| AUF1 | Systemic rheumatic diseases |
| Autologous colon extracted proteins | Crohn's disease |
| Beta2-glycoprotein-I | Antiphospholipid syndrome |
| Blood cell autoantigen | Autoimmune hemolytic anemia |
| Borrelia burgdorferi lysine-enriched protein | Lyme encephalitis |
| Borrelia T cell epitope | Lyme arthritis |
| BP180 | Bullous pemphigoid |
| BPAg2 | IgA disease |
| C1D | Polymyositis-scleroderma overlap syndrome |
| Collagen, preferably Type V collagen | Idiopathic pulmonary fibrosis |
| Cytochrome P450 1A2 | Hepatitis graft-versus-host disease |
| Cytokeratin-10 | Lyme arthritis |
| Deamidated gliadin peptide | Celiac disease |
| Desmocollin 1 | Pemphigus |
| Desmoglein 1 | Pemphigus foliaceus |
| Desmoglein 1 and 3 | Pemphigus |
| Desmoglein 1 and 3 | Pemphigus vulgaris |
| Desmoglein 1 and 3 | Pustular dermatosis (Sneddon-Wilkinson disease) |
| Desmoglein 3 ectodomain | Pemphigus vulvaris |
| Desmoglein-3 peptides | Pemphigus vulgaris |
| Enolase and arrestin | Multiple sclerosis |
| GAD65 | Type 1 diabetes |
| Glatiramer acetate | Multiple sclerosis |
| Globular domain of human C1q | Systemic lupus erythematosus |
| Glutathione S-transferase theta 1 | Primary sclerosing cholangitis |
| GPI-anti-oxLDL/beta2GPI | SLE |
| Heat shock proteins | Carotid atherosclerosis |
| Heparin | Thrombocytopenia |
| Histidyl-transfer RNA synthetase | Jo-1 autoantibody-associated myositis |
| hnRNP A/B proteins | Systemic rheumatic diseases and hnRNP L |
| hnRNP-A2 (RA33) | Pristane-induced arthritis |
| HRES-1 endogenous retrovirus | Systemic lupus erythematosus |
| Hsp60 | Juvenile dermatomyositis |
| hsp60, -65 and -70 | Juvenile idiopathic arthritis |
| Human insulin | Diabetes mellitus type I |
| Human intestinal antigens | Crohn's disease |
| Intrinsic factor | Autoimmune gastritis |
| Jo-1 or Ro-52/Ro 60 | Myositis patients |
| Ku | Connective Tissue |
| Lens proteins | Uveitis |
| MBL | RA |

TABLE 1-continued

| Antigen | Disease |
|---|---|
| Megalin | Donnai-Barrow and faciooculo-acoustico-renal syndromes |
| Myelin basis protein peptides | Multiple Sclerosis |
| Neurofascin | Autoantibody-mediated axonal injury |
| Neuron-specific enolase | Sudden acquired retinal degeneration syndrome |
| Noncollagenous 1 and 2 domains of type VII collagen | Childhood epidermolysis bullosa acquisita |
| Noncollagenous domain of type VII collagen | Herpes gestationis |
| Nuclear ribonucleoprotein A2 (hnRNP-A2) | Systemic lupus erythematosus |
| Nucleosome antigen | Lupus erythematosus |
| Nucleosomes | Lupus nephritis |
| p200 | Pemphigoid |
| p200 pemphigoid antigen | Epidermolysis bullosa acquisita |
| Parotid antigens | Sjögren's syndrome |
| Pemphigus vulgaris IgG | Acantholysis |
| Phenylalanyl transfer RNA synthetase | Polymyositis |
| Plasma membrane autoantigens | Autoimmune hepatitis |
| Poly (ADP-ribose) polymerase 1 | Systemic lupus erythematosus |
| Rabaptin 5 as a novel autoantigen | Alzheimer's disease |
| RAP and megalin | Heymann nephritis |
| Recombinant 70 kDa ribonuceloprotein | Mixed connective tissue diseases |
| Red blood cells as model antigens | Autoimmunity |
| Retinal antigen | Macular degeneration |
| Retinal Soluble Antigen | Uveitis |
| Ribosomal P protein | Systemic lupus erythematosus |
| Ribosomal P Protein PO | Mixed connective tissues |
| RNA helicase A | Systemic lupus erythematosus |
| Selenium binding proteins | Behcet's disease |
| Sm | Systemic lupus erythematosus |
| Smd 183-119-autoantigen | SLE |
| Spinal cord cells | Amyotrophic lateral sclerosis (ALS) |
| Squamous Cell Carinoma Antigen Protein Family | Psoriasis |
| SSA/SSB antibodies | Systemic lupus erythematosus |
| Subunit of RLIP76 | Immune-mediated vascular diseases and atherosclerosis |
| Testis-expressed protein TSGA10 | Autoimmune polyendocrine syndrome type I |
| TG3 | Celiac disease |
| Thyroid hormone | Autoimmune encephalopathy |
| Thyroid peroxidase | Type 1 diabetes |
| Transglutaminase | Dermatitis herpetiformis and celiac sprue |
| TRIM proteins | Sjögren syndrome |
| Type I collagen | Systemic sclerosis (Scleroderma) |
| Type I collagen | Idiopathic Pulmonary Fibrosis |
| Type II collagen | RA |
| Type III collagen | Systemic sclerosis (Scleroderma) |
| Type III collagen | Idiopathic Pulmonary Fibrosis |
| Type V collagen | Idiopathic Pulmonary Fibrosis |
| Vimentin | RA |
| ZnT8 (Slc30A8) | Human type 1 diabetes |

The invention claimed is:

1. A method of diagnosing impaired oral immune tolerance in a human susceptible to a disease and treating the human by inducing oral immune tolerance, the method comprising
   a. obtaining a sample from the human;
   b. detecting whether SEQ ID NO: 1 is present in the sample,
   c. diagnosing the human as having susceptibility to oral immune tolerance induction when SEQ ID NO: 1 is absent from the sample, and
   d. inducing oral immune tolerance in the human by administering an effective amount of at least one orally administered antigen to the human.

2. The method of claim 1, wherein detecting whether SEQ ID NO: 1 is present in the sample comprises using fluorescence in situ hybridization (FISH).

3. The method of claim 1, wherein said disease is selected from the group consisting of asthma, Crohn's disease, Celiac disease, multiple sclerosis, idiopathic pulmonary fibrosis, and rheumatoid arthritis.

4. The method of claim 1, wherein said disease is a sclerotic disease.

5. The method of claim 4, wherein said sclerotic disease is systemic sclerosis.

6. The method of claim 1, wherein said sample is selected from the group consisting of: whole blood, blood plasma, urine, tears, semen, saliva, buccal mucosa, interstitial fluid, lymph fluid, meningeal fluid, amniotic fluid glandular fluid, sputum, feces, perspiration, mucous, vaginal secretion, cerebrospinal fluid, hair, skin, fecal material, wound exudate, wound homogenate, and wound fluid.

7. The method of claim 6, wherein said at least one orally administered antigen is a collagen.

8. The method of claim 7, wherein said collagen is selected from the group types consisting of: I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, and XXVIII.

* * * * *

SEQUENCE LISTING

<160> NUMBER OF SEQ ID NOS: 21

<210> SEQ ID NO 1
<211> LENGTH: 33
<212> TYPE: DNA
<213> ORGANISM: Homo sapiens

<400> SEQUENCE: 1
tttttttttt gtacctagtt ctatggttac ctt                33

<210> SEQ ID NO 2
<211> LENGTH: 33
<212> TYPE: DNA
<213> ORGANISM: Homo sapiens

<400> SEQUENCE: 2
tttttttttt gtacctggtt ctatggttac ctt                                    33

<210> SEQ ID NO 3
<211> LENGTH: 601
<212> TYPE: DNA
<213> ORGANISM: Homo sapiens

<400> SEQUENCE: 3
aaaggcacct catggagaaa gacctctgcc tacctcccca ggcttgcctg acttcatcct       60
catatactag ccacctgcac cccaccaaat aattaacttc tgctagtttc ctggacaccc      120
caagccattg tgtgccttgt tcccttgcta tgatatttcc cctttctgga acacctccat      180
caatgttcca gctcaattat cacctcctac aggaagcctt ccctcatttc ctcctatgcc      240
tatcactcaa gaagtattaa ccacactttt ctctgtgctg tagcttttttt ttttgtacct     300 agttctatgg ttacctttac actgcattgt aacctggtat tcatgggctt atctgtgtcc      360
cctgtggagc tgtcagtctc tgaaaggcca gtgcctactt tatttcctct ctagattcca     420
gcactgagat gatgccaggt gtcagccctc cttggaagcc ttaggaaggt ctctccaatt     480
gccctacccc aaccacaata tagaggacta taaaatgagc acatagtggg aggagacaga     540
gtggttccct gattacatgt atgaacgcag ctagagagag aatatgtcct tccaatgtgg     600
g                                                                      601

<210> SEQ ID NO 4
<211> LENGTH: 601
<212> TYPE: DNA
<213> ORGANISM: Homo sapiens

<400> SEQUENCE: 4
aaaggcacct catggagaaa gacctctgcc tacctcccca ggcttgcctg acttcatcct       60
catatactag ccacctgcac cccaccaaat aattaacttc tgctagtttc ctggacaccc      120
caagccattg tgtgccttgt tcccttgcta tgatatttcc cctttctgga acacctccat      180
caatgttcca gctcaattat cacctcctac aggaagcctt ccctcatttc ctcctatgcc      240
tatcactcaa gaagtattaa ccacactttt ctctgtgctg tagcttttttt ttttgtacct     300 ggttctatgg ttacctttac actgcattgt aacctggtat tcatgggctt atctgtgtcc      360
cctgtggagc tgtcagtctc tgaaaggcca gtgcctactt tatttcctct ctagattcca     420
gcactgagat gatgccaggt gtcagccctc cttggaagcc ttaggaaggt ctctccaatt     480
gccctacccc aaccacaata tagaggacta taaaatgagc acatagtggg aggagacaga     540
gtggttccct gattacatgt atgaacgcag ctagagagag aatatgtcct tccaatgtgg     600
g                                                                      601

<210> SEQ ID NO 5
<211> LENGTH: 310
<212> TYPE: DNA
<213> ORGANISM: Homo sapiens

<400> SEQUENCE: 5
tcaaacccag ctttgactcc agagcctgca ctcttcccat tagatcattc tacatccttt       60
tttgggatgg tttagttgcc aactggggat aaaataaatg gtcttttgaa attctttcca      120
ttgcctggat tctattctcc cttatttgat cccaatattg gccttaacac tgtttagcaa      180

```
tttgttatac tgagaacatg ggttaggaaa caatacaatt tgatgagttt aatgtaaatt      240
gttttcaaac ttaagttctc actcttacta ggtcacaaaa tctcagtgag aaggcacctc      300
agagttcatc                                                             310

<210> SEQ ID NO 6
<211> LENGTH: 126
<212> TYPE: DNA
<213> ORGANISM: Homo sapiens

<400> SEQUENCE: 6
gatcccacaa tcgcataaag tcaagtactt gggaccaatt gctccttttc aacacacaca       60
cacacacaca cacacacaca cacacacaca cacacacaca gtttctgctt ctctgatgga      120
atgctg                                                                 126

<210> SEQ ID NO 7
<211> LENGTH: 255
<212> TYPE: DNA
<213> ORGANISM: Homo sapiens

<400> SEQUENCE: 7
tggcaaggac agacacaatt aattaattat atattttag atatagtgta gttgtgtgtg        60
tgtgtgtgtg tgtgtgtgtg tgtgtgtgga gagagagaca gaaagaaaga ataattataa     120
gtagttgtaa aaggtatgag gaaaagttca gtagagaagg agatagaaag tgatgtgggc     180
attattttaa agagggctct tggagacagc ctctctgggc gaggttggga ggtatttgag     240
gtgaagcctg gatga                                                      255

<210> SEQ ID NO 8
<211> LENGTH: 253
<212> TYPE: DNA
<213> ORGANISM: Homo sapiens

<400> SEQUENCE: 8
ctttgcagaa cccatgatta tgacagttgt ctctactctc agttaccaaa tgccctgata       60
tttataggct ctctctacag acacaactgc aactgtcctt ctaagagtgg ctacaataaa     120
tcctaaagtc ctgcagcctc agggagggca ggaaaatggt gggggctggc tcaaattcct     180
aaacacacac acacacacac acacacacac acacacacac acacacacac acacacacgc     240
cctctaagac aat                                                        253

<210> SEQ ID NO 9
<211> LENGTH: 33
<212> TYPE: DNA
<213> ORGANISM: Homo sapiens

<400> SEQUENCE: 9
agaccctaat tttaagcgat ctacagtctg gtg                                    33

<210> SEQ ID NO 10
<211> LENGTH: 33
<212> TYPE: DNA
<213> ORGANISM: Homo sapiens

<400> SEQUENCE: 10
agaccctaat tttaagtgat ctacagtctg gtg                                    33

<210> SEQ ID NO 11
<211> LENGTH: 33
```

<212> TYPE: DNA
<213> ORGANISM: Homo sapiens

<400> SEQUENCE: 11
agagggacaa tgggaccaca taattgaagt tgg                        33

<210> SEQ ID NO 12
<211> LENGTH: 33
<212> TYPE: DNA
<213> ORGANISM: Homo sapiens

<400> SEQUENCE: 12
agagggacaa tgggactaca taattgaagt tgg                        33

<210> SEQ ID NO 13
<211> LENGTH: 33
<212> TYPE: DNA
<213> ORGANISM: Homo sapiens

<400> SEQUENCE: 13
ttctcactct attgcacgga atatatagta ttt                        33

<210> SEQ ID NO 14
<211> LENGTH: 33
<212> TYPE: DNA
<213> ORGANISM: Homo sapiens

<400> SEQUENCE: 14
ttctcactct attgcatgga atatatagta ttt                        33

<210> SEQ ID NO 15
<211> LENGTH: 33
<212> TYPE: DNA
<213> ORGANISM: Homo sapiens

<400> SEQUENCE: 15
cctcacagaa tttacactgg agcctaagta aca                        33

<210> SEQ ID NO 16
<211> LENGTH: 33
<212> TYPE: DNA
<213> ORGANISM: Homo sapiens

<400> SEQUENCE: 16
cctcacagaa tttacattgg agcctaagta aca                        33

<210> SEQ ID NO 17
<211> LENGTH: 33
<212> TYPE: DNA
<213> ORGANISM: Homo sapiens

<400> SEQUENCE: 17
gcaaagccaa ggtacaaact cacgtgcatt aaa                        33

<210> SEQ ID NO 18
<211> LENGTH: 33
<212> TYPE: DNA
<213> ORGANISM: Homo sapiens

<400> SEQUENCE: 18
gcaaagccaa ggtacagact cacgtgcatt aaa                        33

<210> SEQ ID NO 19

```
<211> LENGTH: 33
<212> TYPE: DNA
<213> ORGANISM: Homo sapiens

<400> SEQUENCE: 19
tatcatggca ctcagtctgg tgggtattac tgt                                33

<210> SEQ ID NO 20
<211> LENGTH: 33
<212> TYPE: DNA
<213> ORGANISM: Homo sapiens

<400> SEQUENCE: 20
tatcatggca ctcagtgtgg tgggtattac tgt                                33

<210> SEQ ID NO 21
<211> LENGTH: 33
<212> TYPE: DNA
<213> ORGANISM: Homo sapiens

<400> SEQUENCE: 21
tttttttttt gtacctrgtt ctatggttac ctt                                33
```